United States Patent [19]
Eswara et al.

[11] Patent Number: 5,780,051
[45] Date of Patent: Jul. 14, 1998

[54] METHODS AND ARTICLES OF MANUFACTURE FOR NICOTINE CESSATION AND MONITORING NICOTINE USE

[75] Inventors: Amruta R. Eswara, Beverly; Neal Muni, N. Reading; F. Howard Schneider, Yarmouth; Peter J. Mione, Abington, all of Mass.

[73] Assignee: DynaGen, Inc., Cambridge, Mass.

[21] Appl. No.: 779,281

[22] Filed: Jan. 22, 1997

Related U.S. Application Data

[63] Continuation-in-part of Ser. No. 487,853, Jun. 7, 1995, abandoned, and Ser. No. 881,740, May 7, 1992, which is a division of Ser. No. 135,847, Oct. 13, 1993, Pat. No. 5,403,595, which is a division of Ser. No. 415,859, Apr. 3, 1995, Pat. No. 5,536,503, which is a division of Ser. No. 145,203, Oct. 28, 1993, Pat. No. 5,414,005, which is a division of Ser. No. 862,051, Apr. 2, 1992, abandoned, which is a division of Ser. No. 137,687, Oct. 15, 1993, abandoned, which is a division of Ser. No. 279,619, Jul. 25, 1994.

[51] Int. Cl.[6] .................... A61K 9/70; A61K 9/48; A61K 9/50; A61F 2/02
[52] U.S. Cl. .................... 424/449; 424/423; 424/425; 424/426; 424/451; 424/501; 424/502; 514/810; 514/811; 514/812; 514/813; 514/953; 514/955; 514/963; 514/965
[58] Field of Search .................... 424/423, 425, 424/426, 449, 451, 501, 502; 514/810, 811, 812, 813, 953, 955, 963, 965

[56] References Cited

U.S. PATENT DOCUMENTS

| | | | |
|---|---|---|---|
| 3,789,840 | 2/1974 | Rosenblatt | 128/260 |
| 3,862,946 | 1/1975 | Havera | 260/293 |
| 3,879,555 | 4/1975 | Pachter et al. | 424/260 |
| 3,885,027 | 5/1975 | Shaw et al. | 424/44 |
| 3,887,699 | 6/1975 | Yolles | 424/19 |
| 3,906,100 | 9/1975 | Havera | 424/267 |
| 3,947,592 | 3/1976 | Grosz | 424/330 |
| 3,966,940 | 6/1976 | Pachter et al. | 424/260 |
| 3,976,071 | 8/1976 | Sadek | 128/260 |
| 3,980,766 | 9/1976 | Shaw et al. | 424/10 |
| 4,144,228 | 3/1979 | Jones et al. | 260/112.5 |
| 4,145,435 | 3/1979 | Szmuszkovicz | 424/274 |
| 4,177,056 | 12/1979 | Mueller et al. | 71/83 |
| 4,192,827 | 3/1980 | Mueller et al. | 525/123 |

(List continued on next page.)

FOREIGN PATENT DOCUMENTS

| | | |
|---|---|---|
| 914065 | 11/1972 | Canada . |
| 1273878 | 9/1990 | Canada . |
| 0272918 | 6/1988 | European Pat. Off. . |
| 280413 | 8/1988 | European Pat. Off. . |
| 2369845 | 6/1978 | France . |
| 1911112 | 9/1970 | Germany . |
| 1-197435 | 1/1988 | Japan . |
| 389829 | 3/1965 | Switzerland . |
| 1017032 | 1/1966 | United Kingdom . |
| 1056214 | 1/1967 | United Kingdom . |

OTHER PUBLICATIONS

Davison et al., "Lobeline and Reduction of Smoking", *Psychological Report*, (1972), 31(2): 443–ABSTRACT.

Langone, J., et al., "Monoclonal Antibody Elisa for Cotinine in Saliva and Urine of Active and Passive Smokers", *J. Immuno Methods* . (1988) 114:73–78.

Langone, J., et al., "Nicotine and its Metabolites. Radioimmunoassays for Nictotine and Cotinine", *Biochem.* . (1973). 12:24.

(List continued on next page.)

*Primary Examiner*—Carlos Azpuru
*Attorney, Agent, or Firm*—Wolf, Greenfield & Sacks, P.C.

[57] ABSTRACT

The present invention features methods and articles of manufacture for treating nicotine withdrawal symptoms and promoting smoking cessation. The methods and articles feature the administration of an effective amount of a nicotine substitute and monitor the presence of nicotine in the biological sample of such subject with a nicotine detection system.

28 Claims, 4 Drawing Sheets

5,780,051

Page 2

U.S. PATENT DOCUMENTS

| | | | |
|---|---|---|---|
| 4,248,855 | 2/1981 | Blank et al. | 424/19 |
| 4,277,582 | 7/1981 | Mueller et al. | 525/421 |
| 4,304,591 | 12/1981 | Mueller et al. | 71/93 |
| 4,344,431 | 8/1982 | Yolles | 128/260 |
| 4,361,553 | 11/1982 | Loh et al. | 424/177 |
| 4,380,550 | 4/1983 | Kleinlogel et al. | 424/324 |
| 4,444,758 | 4/1984 | Scherschlicht et al. | 424/177 |
| 4,464,378 | 8/1984 | Hussain | 424/260 |
| 4,592,753 | 6/1986 | Panoz | 604/897 |
| 4,620,977 | 11/1986 | Strahilevitz | 424/88 |
| 4,632,935 | 12/1986 | Kaplan | 514/429 |
| 4,634,665 | 1/1987 | Nuwayser | 604/307 |
| 4,635,651 | 1/1987 | Jacobs | 131/271 |
| 4,698,342 | 10/1987 | Crosby | 514/253 |
| 4,719,215 | 1/1988 | Goldberg | 514/282 |
| 4,745,160 | 5/1988 | Churchill et al. | 525/415 |
| 4,749,576 | 6/1988 | Lee et al. | 424/486 |
| 4,767,628 | 8/1988 | Hutchinson | 424/426 |
| 4,789,726 | 12/1988 | Hutchinson | 528/354 |
| 4,822,617 | 4/1989 | Panoz | 424/449 |
| 4,834,973 | 5/1989 | Strahilevitz | 424/85.8 |
| 4,873,086 | 10/1989 | Good et al. | 424/409 |
| 4,898,734 | 2/1990 | Mathiowitz et al. | 424/426 |
| 4,908,213 | 3/1990 | Govil et al. | 424/447 |
| 4,920,989 | 5/1990 | Rose et al. | 131/270 |
| 4,927,676 | 5/1990 | Heiber et al. | 424/449 |
| 4,935,428 | 6/1990 | Lewis | 514/282 |
| 4,943,435 | 7/1990 | Baker et al. | 424/448 |
| 4,956,391 | 9/1990 | Sapse | 514/810 |
| 4,963,367 | 10/1990 | Ecanow et al. | 424/485 |
| 4,971,079 | 11/1990 | Talapin et al. | 131/359 |
| 4,994,260 | 2/1991 | Källstrand et al. | 424/10 |
| 4,996,047 | 2/1991 | Kelleher et al. | 424/79 |
| 5,030,216 | 7/1991 | Theeuwes et al. | 604/892 |
| 5,055,478 | 10/1991 | Copper et al. | 514/343 |
| 5,334,390 | 8/1994 | Solomon et al. | 424/439 |

OTHER PUBLICATIONS

Rubin, S., et al., "Determination of Blood Plasma Levels of Hydrazine Derivatives of Isonicotine Acid", *Dis. Chest.*, (1952), 21:439.

Nielsch and Giefer, *Arzneimittel–Forschung*, (1959), 9:636.

Nielsch and Giefer, *Arzneimittel–Forschung*, (1959), 9:700.

Derwent File Supplier WPI(L), AN=89-273364 [38], Derwent Publications Ltd. London, GB. & JPA. 1197435 (Teikoku Seiyaku K.K.), Sep. 9, 1989.

Deasy, P.B., "Microencapsulation and Related Drug Processes," *Marcel Dekker, Inc.*, New York, (1984), pp. 223–224.

Belles, Q., et al., "A Sensitive Filler Paper Spot Test for the Detection of Isoniasid (INH) Metabolities in Urine", *Med. J. of Australia*, (1962), 2:588.

Kasik, J.E., et al., "A Simple Test to Determine Whether a Patient is Taking Isoniazid", *Amer. Rev. Resp. Dis.*, (1962), 85:282.

Kilburn, J., et al., "Reagent–Impregnated Paper Strips for Detection of Niacin", *Amer. J. Clinical. Path.*, (1968), 38:530.

Kilburn, et al., "Reagent–Impregnated Paper Strip for Detection of Isoniazid in Urine", *Amer. Rev. Resp. Dis.*, (1972), 106:923.

Stanley, J., et al., "An Investigation of Dapsone Compliance Using an Isoniazid–Marked Formulation", *Leprosy Review*, (1983) 54:317.

Peach, et al., "Simple, Inexpensive Urine Test of Smoking", *Thorax*, (1985), 40:351.

Barlow, R., et al., "The Direct Barbituric Acid Assay for Nicotine Metabolites in Urine: A Simple Colorimetric Test for the Routine Assessment of Smoking Status and Cigarette Smoke Intake", *Clinica. Chemica. Acta.*, (1987) 165:45.

Kolonen, S., et al., "Assessment of the Automated Colorimetric and the High Performance Liquid Chromatographic Methods for Nicotine Intake by Urine Samples of Smokers Smoking Low–and Medium–Yield Cigarettes" *Clinica. Chemica. Acta.*, (1987), 170:225.

Kullberg, M., et al., "Studies on the Single Extraction of Amphetamine and Phenobarbital from Urine Using XAD–2 Resin". *Biochem. Med.*, (1973), 7:323–335.

Mule, S.J., et al., "Routine Identification of Drugs of Abuse in Human Urine", *J. of Chrom.* (1971), 63:289–301.

Miller, W.L., et al., "Studies on the Quantitative Extraction of Morphine from Urine Using Nonionic XAD–2 Resin", *Biochem. Med.* (1973), 7:145–158.

Kullberg, M.P., et al., "Studies on the Use of XAD–2 Resin for Detection of Abused Drugs in Urine", *Clinic. Chem.* (1974), 20:2, 177.

Watson, I., "Rapid Analysis of Nicotine and Cotinine in the Urine of Smokers by Isocratic High–Performance Liquid Chromatography", *J. Chroma.* (1977), 143:203–206.

Kyerematen, G., et al., "Smoking–Induced Changes in Nicotine Disposition: Application of a New HPLC Assay for Nicotine and its Metabolites", *Clin. Phar. Ther.*, (1982), 32:769.

Jacob, P., et al., "Improved Gas Chromatographic Method for the Determination of Nicotine and Cotinine in Biologic Fluids", *J. of Chroma.*, (1981), 222:61–70.

Hengen, N., et al., "Gas–Liquid Chromatographic Determination of Nicotine and Cotinine in Plasma", *Clin. Chem.*, (1978), 24/1:50–53.

Feyerabend, C., "Rapid Gas–Liquid Chromatographic Determination of Cotinine in Biological Fluids", *Analyst*, (1980), 105:998.

Knight, G., et al., "Improved 125I Radioimmunoassay for Cotinine by Selective Removal of Bridge Antibodies", *Clin. Chem.*, (1985), 31/1:118–121.

Puhakainen, E., "An Automated Colorimetric Assay for Urine Nicotine Metabolites: A Suitable Alternative to Cotinine Assays for the Assessment of Smoking Status" *Clinca. Chemica. Acta.*, (1987), 170:255–262.

Yamasaki, E., "Concentration of Mutagens from Urine by Adsorption with Nonpolar Resin XAD–2: Cigarette Smokers have Mutagenic Urine", (1977), *Proc. Natl. Acad. Sci.*.

Henderson, W., "The Development and use of the Potts–Cozart Tube Test for the Detection of Isoniazid (INH) Metabolites in Urine", (1986) *Jrnl. Arkansas Med. Soc.*.

Young, W., et al., "Development of a Paper Strip Test for Detection of Niacin Produced by Mycobacteria", *Applied Microbiology*, (1970) 20/6:939–945.

Watts, R., et al., "Continine Analytical Workshop Report: Consideration of Analytical Methods for Determining Cotinine in Human Body Fluids as a Meaure of Passive Exposure to Tobacco Smoke", *Enviro, Health Persp.*, (1990), 84:173–182.

Biercke, R., et al., "Stereospecific Monoclonal Antibodies to Nicotine and Cotinine and Their Use in Enzyme–Linked Immuno–Sorbent Assays", (1986), *Jrnl. Immuno. Methods*, 90:203–213.

Jacob, P., et al., "Oxidative Metabolism of Nicotine in Vivo", *Advances in Pharmacological Science*, (1991), 35–44.

Parviainen, M., et al., "Nicotine Metabolites in the Urine of Smokers", *Jrnl. of Chromo.* (1990) 525:193–202.

Kyerematen, G., et al., "Disposition of Nicotine and Eight Metabolites in Smokers and Nonsmokers:Identification in Smokers of Two Metabolites are No Longer Lived Than Cotinine", *Clin, Pharmacol. Ther.*, (1990), 641–651.

Jacob, N., et al., "Measurment of Urinary Tobacco Markers in a Smoking–Cessation Program". Clinical Chemistry, (1991), 37/9:1655.

Takanashi, S., et al., "Adriamycin Metabolism in Man, Evidence From Urinary Metabolites", *Drug Metabolism and Disposition*, (1976), 4/1:79.

Burnham, A.K., et al., "Identification and Estimation of Neutral Organic Contaminants in Potable Water", *Institute for Atomic Research and Dept of Chem.*

Cox, P., et al., "Novel Metabolic Products of Cyclophosphamide in Human Urine", *Biochem, Pharma.*, (1975) 24:1233–1235.

Smith, C.L., et al., "Evaluation of Diethylthiobarbituric Acid as a Spectrophotometric Reagent for Tobacco Alkaloids", *The Analyst*, (1987), 112:11:1515–1518.

Barlow, R.D., et al., "The Direct Barbituric Acid Assay for Nicotine Metabolites in Urine: A Simple Colorimetric Test for the Routine Assessment of Smoking Status and Cigarette Smoke Intake", *Clinica Chimica Acta.*, (1987), 165:1:45–52.

Dorsey, J., "Control of the Tobacco Habit", *Ann. Int. Medicine*. (1936), 10:628–631.

Hoffstaedt, E., "The Use of Lobeline in the Treatment of Smokers", *The Medical J. of Australia*, (Feb. 24, 1964).

Kalyuzhnyy, V.V., [Engish Translation of Russian Original], *J. Of Neural Psychiat.*, (1968) 68:1864–1870.

London, S.J., "Clinical Evaluation of a New Lobeline Smoking Deterrent", *Current Therapeutic Res.*, (1963), 5:167–175.

Perlstein, I.B., "Symposium on Recent Advances in the Medical Aspects if Smoking", *The Matthew Publish. Co., NY.* (1964), 40–45.

Prignot, J., "Pharmacological Approach to Smoking Cessation", *Eur. Respi. J.*, (1969), 2:550–560.

Swartz, H., "Clinical Evaluation of Smokurb . . ." *Current Therapeutic Research*, (1964), 6:290–296.

Scott, G.W., et al., "Buffered Lobeline as a Smoking Deterrent", *Lancent*, Jan. 6, 1962, 58–59.

Davison, G., et al., "Lobeline and Reduction of Cigarette Smoking", *Psychological Reports*, (1972), 31:443–446.

Merry, J., et al., "The Effect of Buffered Lobeline . . .", *Practitioner*, (1963), 190:628–631.

Rapp, G.W., et al., "A Critical Evaluation of a Lobeline Based Smoking Deterrent", *Amer. J. Med. Sci.*, (1955), 230:9–14.

Rapp, G. W., et al., "Absorption and Utility of Lobeline as a Smoking Deterrent", *Amer. J. Med. Sci.*, (1959), 237:287–292.

Wright, I., et al., "Lobeline Sulfate: Its Pharmacology and Use . . .", *J. Amer. Med. Assn.*, (1937) 109:649–654.

Schuster, C.R., et al., Chapter 8:"The Effects of d–Amphetamine, Meprobate, and Lobeline on the Cigarette Smoking Behavior", (1979).

Mullenix, P., et al., "The Effects of Nicotine and Lobeline on Spontaneous Behavior of Adult Male Rats". *Forsyth Research Institute, Boston, MA, sponsored by DynaGen, Inc., Cambridge, MA*, (1990).

Reavill, C., et al., "High Affinity Binding of [3H](–)–Nicotine to Rat Brain Membranes . . . " *Neuropharmacology*, (1988), 27:235–241.

Sloan, J.W., et al., "The Comparative Binding Characteristics of Nicotinic Ligands . . . " *Pharmacol. Biochem. Behav.* (1988), 30(1):255–267.

Takagi, et al., "Lobeline–Containing Skin Patch to Discourage Tobacco Smoking", *63–6 Pharmaceuticals*, (1989) Abstract.

Package Insert: Cigarrest–Advantage Life Products, Laguna Hills, CA 92653–(1989).

Package Insert: Bantron–JMI–DEP Corporation, Los Angeles, CA 90220.

Package Insert: Smoker's Choice (Gum or Lozenge) –SAPRO, INC., Lincoln, NE 68506–(1990).

Package Insert: Nic–Fit–NIC–FIT Corporation, Plantation, FL 33324.

Orleans, C. T., et al., "Smoking Ban in US Hospitals Presents New Challenges", *Tobacco Control*, (1992), 1:46–47..

Hurt, R.D., et al., "Inpatient Treatment of Severe Nicotine Dependence", *Mayo Clin Proc.* (1992) 67:823–828.

NICOTINE

NICOTINE - 1' - N - OXIDE

NOR - NICOTINE

COTININE

3 - HYDROXY - COTININE

COTININE - N - OXIDE

NOR - COTININE
(DES METHYL COTININE)

3 - HYDROXY - COTININE
GLUCURONIDE

3 - PYRIDYL - CARBINOL

3 - PYRIDYL ACETIC ACID

DEMETHYL - COTININE $\Delta^{T3'}$- ENAMINE

METHODS AND ARTICLES OF MANUFACTURE FOR NICOTINE CESSATION AND MONITORING NICOTINE USE

RELATED APPLICATIONS

This application is a continuation in part of U.S. patent application, Ser. No. 08/487,853, filed Jun. 7, 1995, now abandoned. The application is also a continuation in part of U.S. patent application, Ser. No. 07/881,740, filed May 7, 1992, now abandoned, which is a continuation-in-part of U.S. application Ser. No. 08/135,847, filed Oct. 13, 1993 now U.S. Pat. No. 5,403,595, which is a Divisional application Ser. No. 08/415,859, filed Apr. 3, 1995, now U.S. Pat. No. 5,536,503, which is a division of U.S. application Ser. No. 08/145,203, filed Oct. 28, 1993, now U.S. Pat. No. 5,414,005, which is a divisional of U.S. application Ser. No. 07/862,051, filed Apr. 2, 1992, abandoned, which is a divisional of U.S. application Ser. No. 08/137,687, filed Oct. 15, 1993, now abandoned, which is a divisional of U.S. application Ser. No. 08/279,619, filed Jul. 25, 1994 now abandoned.

BACKGROUND OF THE INVENTION

Greater understanding of the adverse health effects of tobacco consumption and associated nicotine intake has led to a marked increase in research on the nature of nicotine addiction and its treatment. Addiction to nicotine, as described in past U.S. Surgeon General's reports on smoking, is widespread, with over 50 million smokers in the United States alone. Addiction to nicotine is a major barrier to an individual's ability to successfully and permanently stop smoking.

As with other addictions, addiction to nicotine encompasses two key components. One component is a physiological addiction to nicotine itself. The physiological addiction is mediated through adaptive changes in specific brain nicotine receptors that lead to typical withdrawal symptoms upon abstaining from nicotine. A second component is a complex behavioral component. The behavior component is linked to learned internal cues associated with various positive or negative emotional feelings tied to tobacco smoking or abstinence.

The physiological addiction to nicotine is significant. The American Psychiatric Association's Diagnostic and Statistical Manual of Mental Disorders (third edition, revised) lists the officially recognized diagnostic criteria for nicotine withdrawal as the presence of at least four of the following signs: (1) craving for nicotine; (2) irritability, frustration, anger; (3) anxiety; (4) difficulty concentrating; (5) restlessness; (6) decreased heart rate; and (7) increased appetite or weight gain.

Differing approaches to smoking cessation attempt to address the physiological addiction and the behavioral component. The approaches range from stopping "cold turkey," hypnosis, electroshock, acupuncture, behavioral counseling, to various forms of therapeutic support. Nicotine replacement therapies such as chewing gum and transdermal patches, in conjunction with behavioral counselling, are now commonly used to treat nicotine withdrawal and as an aid to smoking cessation. However, long-term success through the use of nicotine replacement is low. In general, 25% or less of the individuals attempting to stop nicotine use are abstaining 12 months after treatment.

Clinicians and epidemiologists often need an accurate assessment of whether and to what extent a person smokes or otherwise uses nicotine. Relying upon self-reporting by nicotine users regarding their nicotine habits is often inaccurate. In addition, clinicians and epidemiologists may require information concerning inhalation of secondary smoke by non-smokers as well as concerning other passive exposure to nicotine as a result of environmental conditions.

Further, many treatments for smoking cessation utilize nicotine. Nicotine is administered through routes other than smoking, for example chewing gum and patches. The treatment of smoking cessation by the administration of nicotine creates problems for the clinician. It may be difficult, if not impossible, to distinguish nicotine or nicotine metabolites which are present due to the therapy from those which are present because the subject is still smoking.

It is also desirable to involve the subject in monitoring his or her performances. However, most assays are not convenient for home use and a subject may have difficulty reading test results which may reflect only partial adherence to a smoking cessation regimen or a regimen which includes the administration of nicotine.

Lobeline is the principal alkaloid obtained from the dried leaves and tops of *Lobelia inflata*, an annual plant of the Lobeliaceae family. Lobeline is a substituted piperidine compound that produces several physiological effects, some of which are similar to those produced by nicotine. It is believed that the pharmacological actions of lobeline are produced by its ability to bind to nicotine receptors in the brain and elsewhere in the body. Lobeline's potency in causing peripheral pharmacological effects, such as increases in blood pressure and heart rate, is significantly less than that of nicotine.

Lobeline has been proposed as a substitute for nicotine, to reduce dependence on nicotine and reduce the use of tobacco products. Although use of lobeline as a smoking cessation aid has been studied since at least the 1930's, its efficacy has been a matter of dispute.

Typical over-the-counter (OTC) products providing lobeline comprise Nicoban™, Bantron™, CigArrest™, NicFit™ and Smoker's Choice™. All lobeline containing smoking cessation products sold in recent years have been non-prescription OTC products. The FDA reports that all OTC smoking cessation aids are ineffective and has taken the unusual step of declaring all such OTC products mislabelled in order to remove such products from the market. Most of the OTC products administered lobeline orally for absorption in the gastrointestinal tract. The directions with such products recommend a daily dose of up to 6 milligrams. Antacids are incorporated in some of the products to overcome gastrointestinal discomfort, a side-effect similar to that caused by nicotine. Higher oral doses may not be feasible because of the concomitant gastric upset.

Although there have been reports of using lobeline in oral formulations at doses in excess of 10 mg/day, nausea and even vomiting have been associated with such doses. A further problem with such oral dose regimens is that self-administration of as many as 18 tablets per day may have been required. Patients may consider such a dosing regimen as intrusive, and such dosing regimen does not permit the physician to carefully control the administration of the drug or monitor patient compliance.

Lobeline may be poorly absorbed from the gastrointestinal tract. Subjects desiring to substitute lobeline for nicotine are unable to take effective quantities of lobeline orally, due to adverse gastrointestinal effects. The oral products may not produce effective blood or tissue levels.

One product presently available, Smoker's Lozenges, contains lobeline in a candy lozenge. The lozenge is intended to dissolve slowly in the mouth to release lobeline. A second product, Smoker's Gum, contains lobeline in a gum base. The gum is intended to release lobeline slowly as the gum is chewed. The instructions with these products do not instruct users to retain the dissolved candy or gum fluids in the oral cavity. The normal reflex would urge users to swallow, severely limiting any buccal absorption of lobeline. Absorption of swallowed lobeline from the gastrointestinal tract may not avoid first pass metabolism by the liver.

These OTC products, as with other lobeline OTC products, have been subjected to FDA action questioning the efficacy of the formulation. It was believed that effective doses of lobeline could not be obtained without an invasive dosage form, such as injection.

The present invention is directed to methods and articles of manufacture for delivering an effective amount of lobeline and monitoring the smoking cessation with a nicotine detection system. The methods and articles of manufacture of the present invention provide relief from acute nicotine withdrawal, and allow a subject to easily monitor adherences to a smoking cessation program.

SUMMARY OF THE INVENTION

The present invention features methods and articles of manufacture for the treatment of nicotine withdrawal symptoms. One method of the present invention comprises administering to a subject an effective amount of a nicotine substitute prior to or during a period in which the subject is experiencing nicotine withdrawal symptoms and monitoring nicotine use with a nicotine detection system. The nicotine substitute alleviates the subject's desire for nicotine. The nicotine detection system does not measure the presence of the nicotine substitute.

The term "nicotine" refers to the addictive ingredient of tobacco products. Nicotine has the formula represented below:

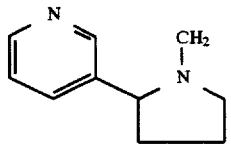

The term "nicotine substitute" refers to either a receptor binding nicotine substitute or a sensory altering nicotine substitute. A nicotine substitute as used herein does not include nicotine.

A "receptor binding nicotine substitute" as used herein is a compound which exhibits an affinity for nicotinic receptor-enriched brain tissue, in in vitro binding assays. Examples of such compounds include lobeline, arecoline, isoarecolone, anabasine and cytisine.

Lobeline, also known as 2-[6-(β-hydroxyphenethyl)-1-methyl-2-piperidyl] acetaminophen has the following structural formula:

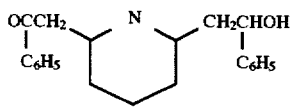

The term "lobeline" as used herein includes lobeline free base and its various salts and lobeline analogs. Functional groups may be added or deleted from the fonnula above, while retaining the physiological activity of lobeline. Such alterations and deviations are encompassed within the term "lobeline analogs".

Arecoline, also known as methyl 1,2,5,6-tetrahydro-1-methylnicotinate has the following structural formula:

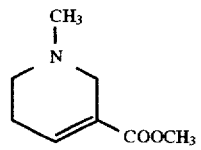

The term "arecoline", as used herein, includes arecoline free base and its various salts and arecoline analogs. Functional groups may be added or deleted from the formula above while retaining the physiological activity of arecoline. Such alterations and deviations are encompassed within the term "arecoline analogs".

Isoarecolone, also known as 1,2,5,6-tetrahydro-1-methyl-4-pyridylmethylketone, has previously been described in the article by Requill et al, entitled "Behavior Effects of the Nicotinic Agonists N-(3 pyridyl-methyl) pyrrolidine and isoarecolone in Rats". Psychopharmacology Berlin (1990), Vol. 102:4 pp. 521–8. Isoarecolone is represented by the formula below:

Anabasine also known as 2-(3-pyridyl) piperidine has the following structural formula:

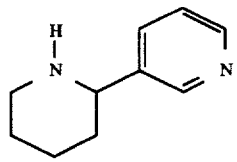

The term "anabasine" as used herein includes anabasine free base and its various salts and anabasiine analogs. Functional groups may be added or deleted from the formula above while retaining the physiological activity of anabasine. Such alterations and deviations are encompassed by the term "anabasine analogs".

Cytisine, also known as 1,2,3,4,5,6-hexahydro-1,5-methano-8H-pyrido-[1,2-a][1.5] diazocin-8-one has the following structural formula:

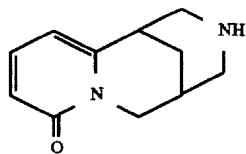

The term "cytisine", as used herein, includes cytisine free base and its various salts and cytisine analogs. Functional groups may be added or deleted from the formula above while retaining the physiological activity of cytisine. Such alterations and deviations are encompassed by the term "cytisine analogs".

A "sensory altering nicotine substitute" as used herein is a compound which when administered to a subject alters the subjects sensory perception such that the subjects awareness of nicotine withdrawal is reduced. Sensory altering nicotine substitutes include anti-anxiety agents, antidepressants, anti-obsessional agents, and antipsychotic agents. Anti-anxiety agents include but are not limited to the following compounds: Adatanserin Hydrochloride; Alpidem; Buspirone Mesylate; Bretazenil; Glemanserin; Ipsapirone Hydrochloride; Mirisetron Maleate; Ocinaplon; Ondansetron Hydrochloride; Panadiplon; Pancopride; Pazinaclone; Serazapine Hydrochloride; Tandospirone Citrate; Zalospirone Hydrochloride.

Antidepressants include but are not limited to the following compounds: Adatanserin Hydrochloride; Adinazolam; Adinazolam Mesylate; Alaproclate; Aletamine Hydrochloride; Amedalin Hydrochloride; Amitriptyline Hydrochloride; Amoxapine; Aptazapine Maleate; Azaloxan Fumarate; Azepindole; Azipramine Hydrochloride; Bipenamol Hydrochloride; Bupropion Hydrochloride; Butacetin; Butriptyline Hydrochloride; Caroxazone; Cartazolate; Ciclazindol; Cidoxepin Hydrochloride; Cilobamine Mesylate; Clodazon Hydrochloride; Clomipramine Hydrochloride; Cotinine Fumarate; Cyclindole; Cypenamine Hydrochloride; Cyprolidol Hydrochloride; Cyproximide; Daledalin Tosylate; Dapoxetine Hydrochloride; Dazadrol Maleate; Dazepinil Hydrochloride; Desipramine Hydrochloride; Dexamisole; Deximafen; Dibenzepin Hydrochloride; Dioxadrol Hydrochloride; Dothiepin Hydrochloride; Doxepin Hydrochloride; Duloxetine Hydrochloride; Eclanamine Maleate; Encyprate; Etoperidone Hydrochloride; Fantridone Hydrochloride; Fenmetozole Hydrochloride; Fenmetramide; Fezolamine Fumarate; Fluotracen Hydrochloride; Fluoxetine; Fluoxetine Hydrochloride; Fluparoxan Hydrochloride; Gamfexine; Guanoxyfen Sulfate; Imafen Hydrochloride; Imiloxan Hydrochloride; Imipramine Hydrochloride; Indeloxazine Hydrochloride; Intriptyline Hydrochloride; Iprindole; Isocarboxazid; Ketipramine Fumarate; Lofepramine Hydrochloride; Lortalamine; Maprotiline; Maprotiline Hydrochloride; Melitracen Hydrochloride; Milacemide Hydrochloride; Minaprine Hydrochloride; Mirtazapine; Moclobemide; Modaline Sulfate; Napactadine Hydrochloride; Napamezole Hydrochloride; Nefazodone Hydrochloride; Nisoxetine; Nitrafudam Hydrochloride; Nomifensine Maleate; Nortriptyline Hydrochloride; Octriptyline Phosphate; Opipramol Hydrochloride; Oxaprotiline Hydrochloride; Oxypertine; Paroxetine; Phenelzine Sulfate; Pirandamine Hydrochloride; Pizotyline; Pridefine Hydrochloride; Prolintane Hydrochloride; Protriptyline Hydrochloride; Quipazine Maleate; Rolicyprine; Seproxetine Hydrochloride; Sertraline Hydrochloride; Sibutramine Hydrochloride; Sulpiride; Suritozole; Tametraline Hydrochloride; Tampramine Fumarate; Tandamine Hydrochloride; Thiazesim Hydrochloride; Thozalinone; Tomoxetine Hydrochloride; Trazodone Hydrochloride; Trebenzomine Hydrochloride; Trimipramine; Trimipramine Maleate; Venlafaxine Hydrochloride; Viloxazine Hydrochloride; Zimeldine Hydrochloride; Zometapine.

Antiobsessional agents include but are not limited to the following compound: Fluvoxamine Maleate.

Antipsychotic agents include but are not limited to the following compounds: Acetophenazine Maleate; Alentemol Hydrobromide; Alpertine; Azaperone; Batelapine Maleate; Benperidol; Benzindopyrine Hydrochloride; Brofoxine; Bromperidol; Bromperidol Decanoate; Butaclamol Hydrochloride; Butaperazine; Butaperazine Maleate; Carphenazine Maleate; Carvotroline Hydrochloride; Chlorpromazine; Chlorpromazine Hydrochloride; Chlorprothixene; Cinperene; Cintriamide; Clomacran Phosphate; Clopenthixol; Clopimozide; Clopipazan Mesylate; Cloroperone Hydrochloride; Clothiapine; Clothixamide Maleate; Clozapine; Cyclophenazine Hydrochloride; Droperidol; Etazolate Hydrochloride; Fenimide; Flucindole; Flumezapine; Fluphenazine Decanoate; Fluphenazine Enanthate; Fluphenazine Hydrochloride; Fluspiperone; Fluspirilene; Flutroline; Gevotroline Hydrochloride; Halopemide; Haloperidol; Haloperidol Decanoate; Iloperidone; Imidoline Hydrochloride; Lenperone; Mazapertine Succinate; Mesoridazine; Mesoridazine Besylate; Metiapine; Milenperone; Milipertine; Molindone Hydrochloride; Naranol Hydrochloride; Neflumozide Hydrochloride; Ocaperidone; Olanzapine; Oxiperomide; Penfluridol; Pentiapine Maleate; Perphenazine; Pimozide; Pinoxepin Hydrochloride; Pipamperone; Piperacetazine; Pipotiazine Palmitate; Piquindone Hydrochloride; Prochlorperazine Edisylate; Prochlorperazine Maleate; Promazine Hydrochloride; Remoxipride; Remoxipride Hydrochloride; Rimcazole Hydrochloride; Seperidol Hydrochloride; Sertindole; Setoperone; Spiperone; Thioridazine; Thioridazine Hydrochloride; Thiothixene; Thiothixene Hydrochloride; Tioperidone Hydrochloride; Tiospirone Hydrochloride; Trifluoperazine Hydrochloride; Trifluperidol; Triflupromazine; Triflupromazine Hydrochloride; Ziprasidone Hydrochloride.

Nicotine withdrawal refers to the clinical symptoms associated with a decreased level of nicotine in the blood of a subject who habitually uses nicotine. The symptoms include but are not limited to (1) cravings for nicotine; (2) irritability, frustration, anger; (3) anxiety; (4) difficulty concentrating; (5) restlessness; (6) decreased heart rate; and/or (7) increased appetite or weight gain.

The term "administering" means applying as a remedy, such as by the placement of a drug in a manner in which such drug would be received and be effective in carrying out its intended purpose.

The term "sublingual" refers to the area of the oral cavity below the tongue. The term "nasal" refers to the air passages extending from the nose to the lungs. The term "mucosa" refers to a mucous membrane. The term "pulmonary tissues" refers to the bronchioles, alveolar ducts and alveoli.

The term "transdermal" refers to transport or movement through the skin. The term "sustained release" refers to a period of one day or greater. A preferred sustained release formulation is an implantable biopolymer. As used herein, "short-term" means within a five minute period of time.

The term "subject" refers to an individual who is to be treated.

The term "dosage form" refers to a pharmaceutical preparation for administering drug to a subject.

Preferably, the nicotine substitute is administered as a soluble salt. In the case of lobeline, soluble salts of lobeline comprise hydrochloride, sulfate or palmoate salts. A preferred soluble salt comprises the hydrochloride or the sulfate salt which are more soluble than the palmoate. Most preferably, the soluble salt is the sulfate salt.

Preferably, the nicotine substitute is administered by an effective dosage form. An effective dosage form comprises a physical constraint modulating system, such as a transdermal patch or subjectable biopolymer such as those disclosed in U.S. patent application Ser. No. 5,403,595. When the nicotine substitute is lobeline the physical constraint modulating system preferably delivers 30 to 400 mg lobeline sulfate or its equivalent per day. When the nicotine substitute is lobeline a preferred dosage form is one which administers lobeline to the nasal or sublingual mucosa or pulmonary tissues.

The nicotine substitute is delivered in an effective amount for reducing the symptoms of nicotine withdrawal. An effective amount of lobeline is 0.6 to 7.5 mg of lobeline free base. This amount of the nicotine substitute provides an effective level of drug through the sublingual or nasal mucosa or pulmonary tissues to alleviate nicotine withdrawal symptoms.

One embodiment of the present method features a nicotine substitute administered as a sublingual tablet. As used herein, the term "tablet" refers to pharmaceutical dosage forms prepared by compressing or molding. Sublingual tablets are small and flat, for placement under the tongue and designed for rapid, almost instantaneous disintegration and release of drug to the sublingual mucosa. As used herein, the term "tablet" specifically excludes gums and lozenge dosage forms. The term "disintegration" means breaking apart and, as used herein, specifically excludes breaking apart caused by chewing, sucking, crushing or grinding in the oral cavity.

Preferably, the sublingual tablets of the present invention disintegrate, to release the nicotine substitute for rapid absorption by the mucosa, within five minutes and, more preferably, within a two minute period of time. The nicotine substitute, released rapidly to the sublingual mucosa, is absorbed and transported to active sites in the brain, mimicking the rapidly increasing nicotine blood levels individuals experience when smoking. Thus, embodiments of the present method are ideally suited for treating acute nicotine withdrawal. Embodiments are also ideally suited to treat transient cravings for nicotine often experienced by smokers treated with long acting nicotine replacement therapy.

Sublingual administration of the nicotine substitute avoids first pass metabolism by the liver. Thus, nicotine substitutes which are absorbed by the mucosa are most effective in addressing withdrawal symptoms.

Preferably the tablet comprises a taste masking flavoring, such as peppermint, spearmint and the like to improve user acceptance.

One embodiment of the present method features the nicotine substitute administered as a liquid. The nicotine substitute is dissolved in the liquid as a soluble salt.

The liquid can be administered as a nasal spray, nasal drops or as a sublingual spray or drops. Administration of the nicotine substitute as a nasal or sublingual spray or drops, allows the nicotine substitute to be rapidly absorbed and avoid first pass metabolism in the liver. The sprays and drops of the present invention can be administered by means of standard spray bottles or dropper bottles adapted for sublingual or nasal administration.

The nicotine substitute administered as a liquid is available for immediate absorption by the mucosa. The nicotine substitute absorbed by the mucosa is transported to active sites in the brain, mimicking the rapidly increasing blood levels individuals experience with nicotine when smoking.

Preferably, when the nicotine substitute has an unpleasant taste the drops and sprays for sublingual use are flavored to mask the unpleasant taste. A preferred flavoring is peppermint or spearmint. Flavoring increases user acceptability.

A further embodiment of the present method features the administration of a nicotine substitute as a fine liquid mist or a fine powder to the pulmonary tissues. Administration of the nicotine substitute to the pulmonary tissues allow the nicotine substitute to avoid first pass metabolism in the liver. The powders of nicotine substitute are preferably administered by devices such as turbo-inhalers and pressurized cartridge devices. Liquids containing nicotine substitute are administered to the pulmonary tissues by fine nebulizers and aerosols.

Administration of the nicotine substitute to the pulmonary tissues allows the nicotine substitute to be rapidly absorbed and avoids first pass metabolism in the liver. The nicotine substitute absorbed by pulmonary tissues mimicks the rapidly increasing blood levels that individuals experience with nicotine when smoking and/or reduces the users awareness of nicotine withdrawal symptoms.

The method features a nicotine detection system which does not produce a positive result in the presence of nicotine substitutes or their metabolites. The detection system is a solid phase containing the required reagents for the nicotine and/or nicotine metabolite assay. These reagents include a color determinant, a buffer, a cyanogen releasing agent and a cyanogen halide forming agent. Preferably, these reagents are arranged in a certain sequence on the solid phase. The buffer permits detection of nicotine and/or nicotine metabolites from samples having a wide range of different pH values. This invention enables not only the detection of nicotine and/or nicotine metabolites from unprocessed biological samples of active nicotine users, but also enables detection of nicotine and/or nicotine metabolites from processed biological samples of nonsmokers passively exposed to nicotine.

Preferably, the step of monitoring the subject for nicotine use is performed by immersing a solid phase containing the assay reagents into a liquid test sample and observing any color change on the solid phase. Preferably, the intensity of the resultant color is compared to at least one standard in which a known quantity of nicotine and/or nicotine metabolites has been assayed. For example, one standard may be selected to correspond to levels of nicotine and/or nicotine metabolites from a biological sample of a heavy smoker, another standard may be selected to correspond to levels from a light smoker, and another standard may be selected for use in assays detecting nicotine resulting from passive smoke, e.g. 100–300 ng/ml.

One embodiment of the present invention features, as an article of manufacture, a dosage form for treating nicotine withdrawal symptoms comprising an effective amount of a nicotine substitute and a plurality of nicotine detection systems. The nicotine substitute is absorbed through the mucosa to alleviate nicotine withdrawal symptoms. The nicotine detection system is used to monitor the subjects' adherence to a smoking cessation program. In one embodiment the plurality of nicotine detection systems is at least 4. According to another embodiment the plurality of nicotine detection systems is at least 6.

One preferred dosage form is a physical constraint modulation system. A preferred physical constraint modulation system is a transdermal patch or an injectable biopolymer of the type disclosed in U.S. Pat. No. 5,403,595. A preferred physical constraint modulation system delivers 30–400 mg lobeline free base or equivalent nicotine substitute per day.

A further preferred dosage form comprises sublingual tablets, and liquids, mists and powders for administering a nicotine substitute to the sublingual or nasal mucosa or pulmonary tissues or systemically to provide access to the nervous system or other biologically responsive tissues. The dosage form administers an amount of nicotine substitute having a potency the equivalent of 0.6 to 7.5 mg of lobeline free base per dose. Preferably, the nicotine substitute is held in the dosage form as a soluble salt.

A preferred dosage form is a sublingual tablet. Preferably, the sublingual tablet disintegrates and releases the nicotine substitute to the sublingual mucosa within a five minute period of time and most preferably within two minutes.

A further embodiment of the article of manufacture features a dosage form as a liquid. The liquid delivers an effective amount of a nicotine substitute to the nasal or sublingual mucosa or the pulmonary tissues.

The liquid formulation is preferably held in a spray bottle, or nasal drop bottle, fine nebulizer, or aerosol mist container, for ease of administration to the nasal mucosa or pulmonary tissues. For applications featuring administration to the sublingual mucosa, liquid formulations may be held in a dropper or spray bottle calibrated to deliver a predetermined amount of a nicotine substitute to the mucosa. Bottles with calibrated sprays or droppers are known in the art.

A further embodiment of the present invention features a dosage form as a powder. The powder is micronized and delivers an effective amount of a nicotine substitute to the pulmonary tissues.

Other useful dosage forms include any methods known in the art for delivering nicotine substitutes to the nervous system or other biologically responsive tissues.

The detection system of the present invention is reliable, easy, quick, and can be carried out by personnel with little or no training. No solutions of liquid reagents are required as the invention is a completely self-contained solid phase. No analyzing equipment is required, as the assay results may be determined by direct visualization of the color of the solid phase. Moreover, this invention permits testing of unprocessed biological samples that have a wide range of different pH values.

The detection system is a solid phase containing the required reagents for the nicotine and/or nicotine metabolite assay. These reagents include a color determinant, a buffer, a cyanogen releasing agent and a cyanogen halide forming agent. Preferably, these reagents are arranged in a certain sequence on the solid phase. The buffer permits detection of nicotine and/or nicotine metabolites from samples having a wide range of different pH values. This invention enables not only the detection of nicotine and/or nicotine metabolites from unprocessed biological samples of active nicotine users, but also enables detection of nicotine and/or nicotine metabolites from processed biological samples of nonsmokers passively exposed to nicotine.

Preferably, the kit contains a packaged solid phase with the assay reagents already applied onto it. Preferably, the kit also contains at least one standard for quality control of the test assay procedures. Preferably, the kit also contains a reference color chart against which the color intensity of the test assay can be compared in order to identify the level of nicotine and/or nicotine metabolites in the test sample. In one embodiment the kit also contains instructions providing information to a user for self-monitoring regarding the use of the solid phase for detecting nicotine and/or nicotine metabolites.

According to another aspect of the invention a method of treating a subject for nicotine withdrawal symptoms is provided. The method involves the step of detecting an initial nicotine level of the subject with a nicotine detection system and establishing and administering to the subject an initial dose of a nicotine substitute that is required to alleviate the nicotine withdrawal symptoms based on the initial nicotine level of the subject. After the initial dose is administered, a second nicotine level of the subject is detected and a second dose of nicotine substitute is established and administered to the subject based on the second nicotine level. In one embodiment the initial dose is administered to the subject for one week before the second nicotine level is established. According to a preferred embodiment the nicotine levels of the subject are detected at a plurality of intervals and the dose of the nicotine substitute is adjusted at a plurality of intervals, if appropriate, after each detection step.

Other features and advantages of the present invention will be apparent from the following description and illustrations which, depict or describe preferred embodiments of the present invention and the principles thereof and what is now considered to be the best mode to apply these principles.

DETAILED DESCRIPTION OF THE INVENTION

The present invention is described in detail as methods and articles of manufacture for the treatment of nicotine withdrawal symptoms and the monitoring of nicotine use.

Figure 1:
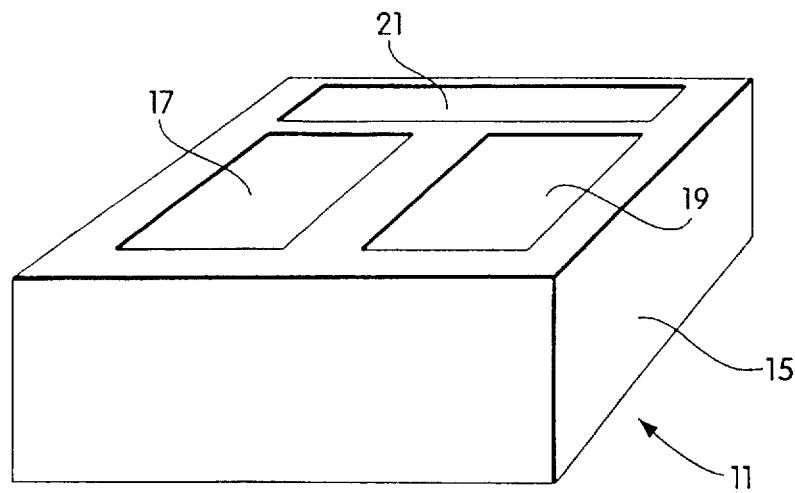
FIG. 1 depicts a kit comprising a dosage form for administering a nicotine substitute and a nicotine detection system.

One embodiment of the present invention features an article of manufacture, a kit, for testing nicotine dependence and for monitoring the subjects compliance. A kit embodying features of the present invention, generally designated by the numeral 11, is illustrated in FIG. 1. Kit 11 is comprised of the following major elements: packaging 15, a dosage form 17, a nicotine detection system 19 and instructions 21. Packaging 15 is a box-like structure for holding dosage form 17, nicotine detection system 19 and instructions 21. Individuals skilled in the art can readily modify packaging 15 to suit individual needs.

Dosage form 17 comprises a nicotine substitute in an effective amount for administering to a subject. Preferably dosage form 17 comprises sublingual tablets, liquids, powders, units or aerosols, or means to apply such nicotine substitutes as liquids, powders, mists or aerosols to the nasal or sublingual mucosa, pulmonary tissue or systemically to other biologically responsive tissues. In the alternative, the dosage form 17 may comprise one or more physical constraint modulation systems (PCMS). Preferred PCMSs comprise transdermal patches and long acting biodegradable polymers. Long acting biodegradable polymers are administered by injection, in which case the dosage form 17 preferably comprises a needle.

Figure 2A:
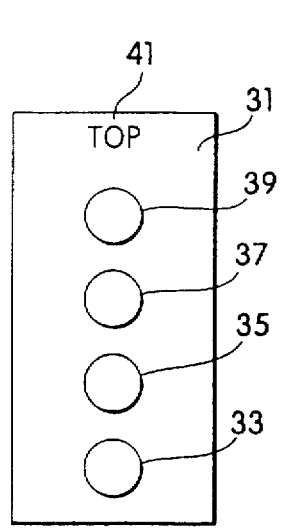
FIG. 2a depicts a test strip embodying features of the present invention.

Nicotine detection system 19 comprises at least one solid phase of the type illustrated in FIG. 2a. Solid phase 31 is a porous strip of paper. Solid phase 31 is implanted with reagents in an order and in discrete areas on the strip. Moving from the bottom to the top of the solid phase 31, the solid phase has a first area 33 impregnated with diethylthiobarbiturate, a second area 35 impregnated with citrate buffer, a third area 37 impregnated with potassium thio cyanate, and a fourth area 39 impregnated with choramine T. Preferably, the strip has a mark 41 designating the top of the strip.

Figure 2B:
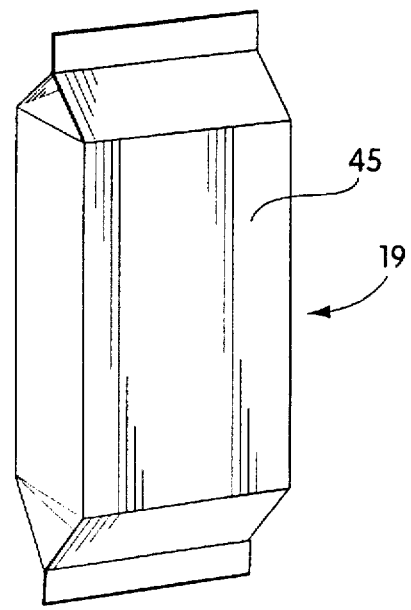
FIG. 2b depicts a plurality of test strips in an envelope.
Figure 3A:
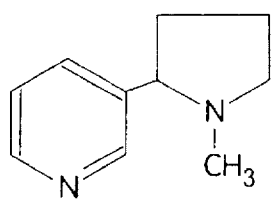
FIG. 3a–k depict known metabolites of nicotine.
Figure 3B:
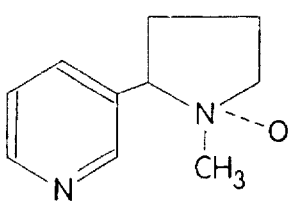
Figure 3C:
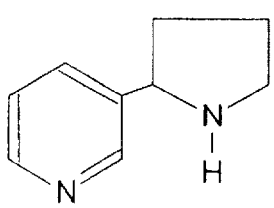
Figure 3D:
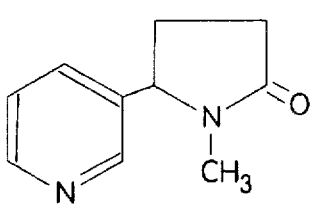
Figure 3E:
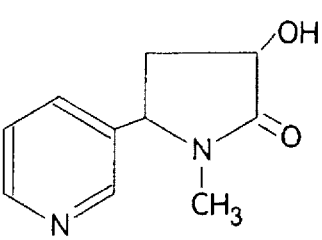
Figure 3F:
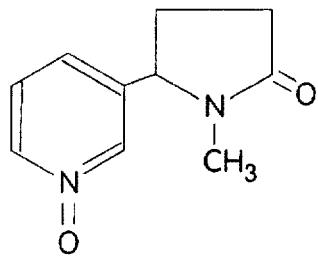
Figure 3G:
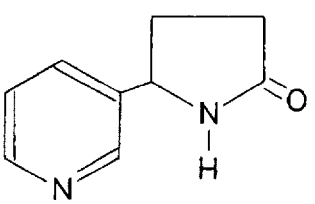
Figure 3H:
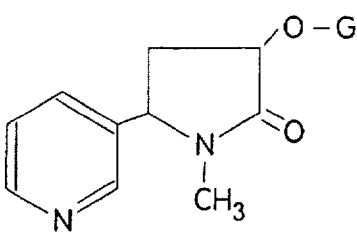
Figure 3I:
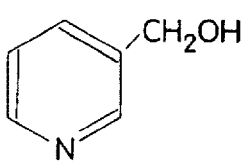
Figure 3J:
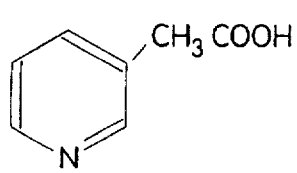
Figure 3K:
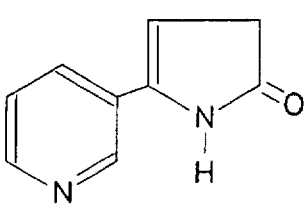

Preferably, the nicotine detection system 19 comprises a plurality of solid phases 31 contained in a foil or plastic envelope 45 as depicted in FIG. 2b.

Instructions 21 include directions for the administration of the dosage form 17 and the nicotine detection system. The instructions 21 may comprise color charts to aid the user in evaluating the color response of the solid phase.

Preferrably, the kit contains at least one standard solution of nicotine and/or nicotine metabolites at a known concentration. These solutions may be used to obtain solid phase (not shown) with a given intensity of color to be used as quality control for the test procedure.

The method of the present invention illustrates the operation of the kit 11. One method of the present invention comprises the step of administering to a subject an effective amount of a nicotine substitute. The nicotine substitute alleviates the subject's desire for nicotine. Nicotine use is monitored by detecting the presence of nicotine in biological samples. such as urine, with a nicotine detection system.

In one embodiment, the administration of the nicotine substitute is with rapid release dosage form. Such rapid release dosage forms comprise sublingual tablets, and sublingual or nasal liquids or liquid mists or micronized powders for application to pulmonary tissues.

The present method and articles of manufacture allow for the immediate or long term dosing of the subject. The subjects may participate in the therapy by monitoring for the presence of nicotine. Coupled with appropriate behavior modification or smoking cessation counseling, the present method and articles of manufacture can be an important part of a smoking cessation program. For instance, the products of the invention may be used in a clinical setting in which a clinician monitors a patients' nicotine level at the outset of the therapy to establish an appropriate dose of the nicotine substitute for alleviating the patients' withdrawal symptoms. The dose of the nicotine substitute that is required for alleviating the symptoms will vary depending on the patients nicotine levels. Throughout the course of the treatment the clinician may monitor the subjects nicotine levels at periodic intervals and adjust the dosage of nicotine substitute required to alleviate the symptoms. Additionally the products of the invention may be used in a home setting as a motivational tool for an individual who is attempting to quit smoking in order to establish a decline in nicotine levels. The individual may periodically monitor his own nicotine levels by using the nicotine detection system of the invention.

Thus one aspect of the invention is a method for using the nicotine detection system of the invention. The method involves the steps of establishing and administering an initial dose of a nicotine substitute, monitoring the nicotine levels after the initial dose and establishing and administering at lest one subsequent dose based upon the monitoring step. Preferably the monitoring step is performed at a plurality of intervals and the dosing is reconsidered and adjusted, if appropriate after each monitoring step.

The nicotine detection system includes a solid phase containing assay reagents including a color determinant, a buffer, a cyanogen releasing agent and a cyanogen halide forming agent.

The term solid phase is intended to include any solid material that is capable of binding the assay reagents and allowing contact of these reagents with a test sample via capillary action. Examples of solid phases include paper, porous membranes, capillary tubes, resin bed (ionic and non-ionic type columns) and the like. The preferred solid phase provides a porous matrix for receiving the biological sample through wicking action. A preferred porous matrix is paper. The paper in the form of a strip has a receiving end for placing in fluids and a wicking end for receiving fluid by capillary action. This capillary action defines a flow of fluid in the strip, referring now to FIG. 2, from the diethyl barbityurate area 33 to the top indicator 41. Examples of paper which may be used in this invention include cellulose, fiberglass and tuff glass. The preferred paper is cellulose. The most preferred paper is 100% cellulose (Absorbent Paper Grade #222; Ahlstrom Filtration Inc., Mount Holly Springs, Pa.).

The solid phase is selected for various functions. The solid phase may be adapted to bind reagents that are applied to the solid phase in solutions. Preferably, the solid phase is adapted to permit movement of liquid through the solid phase by capillary action. A porous solid phase will capture and bind the assay reagents onto the solid phase, and also is adapted to facilitate movement of the reagents through the solid phase by capillary action. The solid phase is selected based on its capacity to hold the reagent volumes applied and on its capillary action properties.

The solid phase can be of any size or shape that will retain the volumes and concentrations of the applied assay reagents. Preferably, the solid phase is flat. Also, preferably, the solid phase is of a sufficient size to allow retention of the multiple assay reagents without overlap between reagents. The solid phase also preferably is of a size and shape that is convenient for immersing a liquid contacting end into a liquid test sample. Also, preferably, the size and shape of the solid phase is large enough to contain sufficient concentrations of reagents so as to permit effective visualization of any color that is formed as an end product of the reaction assay on the solid phase. Examples of shapes which can be used are rectangles, squares, ovals, circles and the like. The preferred solid phase is in the shape of a rectangular strip. The most preferred solid phase is a strip that is on the order of 0.5×7.5 centimeters. Also, preferably, the strip is labelled in some manner to demark the top or bottom of the strip in the embodiment of the invention where the assay reagents have been applied to the strip so that they are arranged in a specific sequence to optimize formation of the colored end product.

The term nicotine and/or nicotine metabolites is intended to include nicotine and derivatives of nicotine that are produced as a result of consumption, e.g., smoking, chewing, inhalation, transdermal delivery, or exposure to a nicotine-containing material or as a result of environmental exposure. Since different people metabolize nicotine at different rates, testing for the presence of any one metabolite of nicotine may not accurately reflect the level of nicotine consumed by an individual. This invention provides a diagnostic assay which detects the presence of nicotine and/or a family of nicotine metabolites, by recognizing the pyridine ring of nicotine and its metabolites. It is the total mix of nicotine and its metabolites which is determinative of the intensity of color formation in the reaction assay of this invention. Examples of nicotine and/or nicotine metabolites which are detected in this invention include nicotine, nicotine-1'-N-oxide, nor-nicotine, cotinine, 3-hydroxy-cotinine, cotinine-N-oxide, nor-cotinine (des methyl cotinine), 3-hydroxy-cotinine glucuronide, 3-pyridyl-carbinol, 3-pyridyl acetic acid and demethyl-cotinine $\Delta 2'3'$-enamine.

The presence of nicotine and/or nicotine metabolites in any liquid sample can be assayed using this invention. The liquid sample can be any liquid susceptible to containing nicotine and/or nicotine metabolites. The sample may serve as a carrier for at least a portion of reagents on the strip allowing them to come into contact with one another such that a reaction occurs. The sample may be unprocessed or processed depending on the sample selected and the amount of nicotine or nicotine metabolite present in the sample. Processing of a sample may include concentration, pH adjustment, filtration, centrifugation, extraction, and the like. In addition to biological samples the liquid samples may also be non-biological samples. An example of a nonbiological liquid is contaminated drinking water. Examples of biological liquid samples include human or animal urine, blood, plasma, serum and saliva. In a preferred embodiment, and one which is used by example herein, the sample is urine. The most preferred sample is unprocessed urine. In particular, the assay can be used to test the urine of a person or animal: Nicotine and nicotine metabolites can be present in the urine of a subject as a result of that subject actively using nicotine, such as by smoking, chewing or otherwise ingesting a nicotine-containing material, or passively, as a result of a subject inhaling smoke produced for example by a different subject smoking nicotine-containing material or by drinking fluid that is contaminated with nicotine or by eating materials contaminated with nicotine. In the case of passive smokers where nicotine and metabolite levels are low, concentration prior to measurement is preferred.

The color determinant is a substance capable of producing a colored end product in the reaction assay of this invention. It is intended to include any compound which reacts with a nicotine intermediate or nicotine metabolite intermediate in the reaction assay of this invention to produce a colored end product. The nicotine intermediate or nicotine metabolite intermediate is formed as a result of a cyanogen halide forming agent reacting with a cyanogen releasing agent to form a cyanogen halide salt, which in turn reacts with the nicotine or nicotine metabolite to form the nicotine intermediate or nicotine metabolite intermediate. The formulas below depict the reaction sequence of a particular nicotine metabolite, cotinine, with the preferred reagents of this invention.

dihydrochloride, O-tolidine dihydrochloride, sulfanilic acid, sulfanilamide, 4-amino-1-naphthalene sulfonic acid, p-amino benzoic acid and 4-amino salicylic acid. The preferred color determinants are barbituate derivatives. Such derivatives include barbituric acid and compounds which are structurally similar to barbituric acid. These structurally similar compounds may be an ester form of the acid (e.g. barbituate) a salt, or may be the acid, ester, or salt substituted with at least one moiety such as a sulfur or an alkyl group. Examples of barbituate derivatives include dimethyl barbituric acid, barbituric acid and diethyl thiobarbiturate. The preferred barbiturate derivative is diethyl thiobarbiturate. (Aldrich Chemical Co., Inc., Milwaukee, Wis.). The concentration of the color determinant may be selected to optimize the intensity of the color of the end product resulting from the assay reaction of this invention. The selection of a concentration of a particular color determinant is interdependent with the concentration of the other assay reagents. For example, a particular concentration of an assay reagent may be fixed to the solid phase and the concentrations of the other assay reagents may be optimized by varying the concentration until a desirable, detectable color is produced at a selected pH.

The term buffer is intended to include any substance over a range of pH values which resists a change in pH when a given increment of $H^+$ or $OH^{3-}$ is added. The presence of a buffer in the reaction assay of this invention permits the

1.

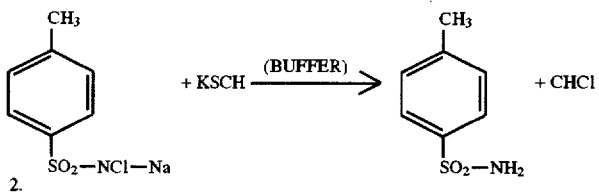

2.

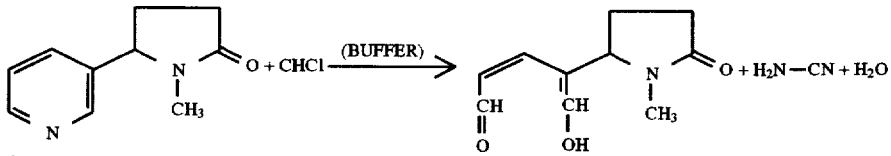

3.

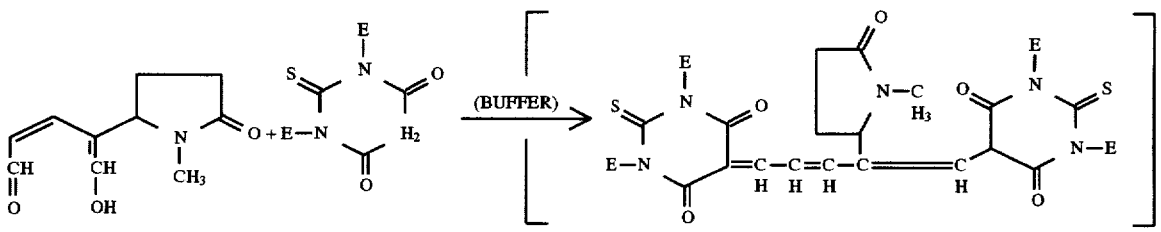

As shown in this reaction, the pyridine ring of cotinine is split by cyanogen chloride and condensed with the color determinant to give a colored end product. The pyridine ring in nicotine and othel nicotine metabolites behaves in a similar fashion.

Examples of color determinants which can be used in this invention include dimethyl barbituric acid, barbituric acid, diethyl thiobarbiturate, 5-amino-2-naphthalene sulfonic acid, 8-amino-2-naphthalene sulfonic acid, 4,5-dihydroxy naphthalene-2,7-disulfonic acid, 7-amino-1,3-naphthalene sulfonic acid monopotassium salt, 1,4-phenylene diamine assay of samples having a wide range of pH values. Unprocessed urine samples typically have a pH between about 4.8 and about 8.2. In testing urine samples, a buffer is selected so that test samples with pH values between about 4.8 and about 8.2 can be effectively assayed. This invention thus permits detection of nicotine and/or nicotine metabolites in an unprocessed urine sample. It should be understood that the type of buffer and the pH of the buffer may be selected based upon such factors as its ability to perform its intended function at a particular pH of the urine. Some buffers, e.g. phosphates, are more appropriate for use with urine samples having high pH's, approximately 8, while others, e.g. aconitate, are more appropriate for use with urine samples having lower pH's, approximately 4.0. Further, the particular pH of the buffer also may be manipulated by one of ordinary skill in the art. Typically, buffers having pH's of less than about 3.5 or greater than about 10 are not as useful as those having a more intermediate pH. For example, some color is observed at all pH's but a pH between 4.1 and about 4.2 is preferred for the citrate buffer. Examples of buffers which may be used in this invention include citrate buffer, acetate buffer, citrate-phosphate buffer, succinate buffer, aconitate buffer, phosphate buffer and carbonate buffer. Examples of molarities and pH values of these buffers which may be used in this invention are listed in Table 1.

TABLE 1

| Buffer | Molarity | pH |
| --- | --- | --- |
| Citrate | 2M | 4.20, 4.43, 4.55, 4.75, 4.94, 5.10 |
| Acetate | 4M | 4.33, 4.63, 4.88, 5.13, 5.36 |
| Citrate-Phosphate | Final concentration is Citric Acid 1M and Phosphate (Dibasic $Na_2HPO_4$) 2M | 4.30, 4.56, 5.10 |
| Phosphate | 0.1M | 5.7, 6.5, 7.0, 8.0 |
| Carbonate | 0.1M | 9.2, 10.0, 10.7 |

For the system described in the examples, the preferred buffer is citrate buffer. The preferred molarity of the citrate buffer is 2M. The preferred pH of the citrate buffer is between about 4.1 and about 4.2.

The term "cyanogen releasing agent" is intended to include any compound which provides cyanogen in a reaction with a particular cyanogen halide forming agent to produce a cyanogen halide salt. Examples of a cyanogen releasing agent which may be used in this invention include potassium thiocyanate, sodiuum thiocyanate, potassium cyanide and sodium cyanide. The preferred cyanogen releasing agent is potassium thiocyanate. (Aldrich Chemical Co., Inc., Milwaukee, Wis.).

The term "cyanogen halide forming agent" is intended to include any compound which provides a halide in a reaction with a particular cyanogen releasing agent to produce a cyanogen halide salt. Examples of a cyanogen halide forming agent which may be used in this invention include chloramine-T and chloramine-B. The preferred cyanogen halide forming agent is chloramine-T. (Aldrich Chemical Co, Inc., Milwaukee, Wis.).

The solid phase contains reagents necessary to detect nicotine and/or nicotine metabolites. The term "contains" is intended to include any application of a reagent onto the solid phase which, after drying, results in the reagent being located on or within the solid phase. Examples of "containing" include impregnation, adsorption, absorption and the like.

The reagents may be applied to the solid phase so that they are arranged in a sequence which maximizes production of the end product in the color reaction assay. The preferred sequences are: (1) color determinant, buffer, cyanogen releasing agent and cyanogen halide forming agent, or (2) color determinant, cyanogen releasing agent, buffer and cyanogen halide forming agent. In either of these arrangements, immersion of one end of the solid phase into a liquid test sample results in the liquid initially making contact with the color determinant. The liquid then sequentially passes of these arrangements, immersion of one end of the solid phase into a liquid test sample results in the liquid initially making contact with the color determinant. The liquid then sequentially passes through the other reagents in the order that they are present on the solid phase, by capillary action. If nicotine or nicotine metabolites are present in the liquid sample, the reactions described above take place, resulting in a colored end product.

This invention also permits the detection of only nicotine and/or nicotine metabolites on a solid phase. The term "only" is intended to mean that the solid phase is designed for the purpose of primarily detecting the pyridine ring in nicotine and/or nicotine metabolites, and is not designed for the purpose of also detecting other chemical constituent groups present on other types of compounds. The term "only," however, may include other cross-reacting compounds which contain a pyridine ring, and which are present in sufficiently high concentration. Preferably, the presence of such cross-reacting compounds is independently determined and corrected for. For example, niacin at therapeutic levels (1–2 gm ingested per day) but not at dietary supplement levels has been shown to give a positive result in the test assay of the invention. Preferably, the person being tested will disclose whether he or she has been ingesting such compounds. Alternatively, the cross-reacting compounds can be eliminated from the urine prior to contacting the urine with the solid phase. For example, an ionic resin column may be used to eliminate ionic cross-reacting compounds.

Niacin (and its metabolites) at therapeutic levels and isoniazid are the only drugs known to show cross-reactivity with a color reaction in an assay using the strip described in the examples below. Other drugs tested with negative cross-reactivity are set forth in lists below.

The following compounds were tested for cross-reactivity with the strip described in the examples below at a concentration of 100,000 ng/ml and unless otherwise noted were found to be non reactive: *Alcohol, *Benzodiazepines, *Cocaine/Metabolites, *Marijuana, *Methadone, *Opiates (Morphine, Heroine), Acetaminophen, Alprazolam, Amitriptyline, Amobarbital, Amoxicillin, Asp-Phemethylester (aspartame), Atenolol, Atropine Sulfate, AZT (3'Azido-3'-Deoxythymidine), Barbital, Benzilic acid β-diethyl-aminoethyl ester, Benzoylecgonine, Brompheniramine, Bupivacaine, Buspirone, Butethal, Caffeine, Cephaloridine, Chloramphenicol, Chloroquine, Chlorpheniramine, Chlorpromozine, Chlorpropamide, Chlorthiazide, Chlorzoxazone, Cimetidine, Ciprofloxacin, Clemastine, Clindamycin, Clonidine, Cocaine Hcl, Codeine, Codeine Sulfate, Cortisone, Cyclizine, Cyclobenzaprine, Cyproheptadine, Desmethylydiazepam, Dextromethorphan, Diazepam, Dibucaine, Digaxin, Diphenhydramine, Diphenoxylate, Dipyridamole, Doxylamine, Ephedrine Sulfate, Epinephrine, *Fenoprofen, Fentanyl, 5-Hydroxyindole-3-acetic acid, 5-Hydroxyindole-2-carboxylic acid, 5-(p-hydroxyphenyl)-5-phenylhydentoine, 5-Hydroxytryptamine, 5-Pregnen-3-ol-20-one, acetate, Flurazepam, Flurbiprofen, Furosemide, 4-Dimethylaminopyrine, Glutethimide, Guaiaco glyceryl ether, Haloperidol, Hippuric acid, Histamine, Hydralazine, Hydrochlorothiazide, Hydroxyzine, I-Amphetamine, Ibuprofen, Indole-3-butyric acid, Indomethacin, Iproniazid, Ketoprofen, Labetalol, Loperarnide, Meprobamate, Methadone, Methadone Hcl, Methamphetamine, Methapyrilene, Methsuximide, Methyprylon, Metrondazole, Methylphenidate, Morphine Sulfate, Morphine-3-β-D-Glucuronide, Nalidixic acid, Naphazoline Hcl, Naproxen, Nifedipine, Norethindrone, Norfloxacin, n-norpropoxyphene, Nortriptyline, Nortryptaline, Orotic Acid, Oxazepam, Oxymetazoline, Pemoline, Penicillin G, Pentobarbital, **Pheniramine, maleate, Phencyclidine, Phenmethazine, Phenobarbital, Phenylpropanolamine, Pheobarbital, Piroxicam, Prazosin, Procaine Hcl, Promethazine, Propanolol, Propoxyphene, Pseudo-ephedrine, Quinidine, Hcl, Ranitidine, Hcl, Secobarbital, Sulfamethoxazole, Tetrahydrozoline, Triprolidine Hcl, Tryptamine.

(*Urine samples from drug abusers. No cross-reactivity at 50,000 ng/ml. *Tested at 500,000 ng/ml. ****Tested at 1,000,000 ng/ml.)

The following over-the-counter drugs were also found to have no cross-reactivity with the reagent impregnated test strip: Vicks Formula 44-D Syrup (Cough Syrup), Cepacol (New, Dry Throat Lozenges), Cepacol (Original, Dry Throat Lozenges), Actifed (Tablets, Head Cold and Allergy), Triaminicol Syrup (Multi-Symptom, Relief, Cough, Cold, Runny Nose), CVS Sore Throat Lozenges (Sore Throat), Surbex-T (Treatment of Vitamin Deficiency), Dimetapp Extent-Tablets (Anti-Histamine, Nasal De-congestant), Benylin Syrup (Cough), Tylenol Extra Strength(Pain Relief Gel Cap), Chloraseptic Spray (Sore Throat Advanced Formula), Advil (Pain Killer), Peptobismol Tablets (Upset Stomach), CVS Nasal Decongestant (Nasal Decongestant Tablets), Chloraseptic Tablets (Sore Throat), Tylenol Allergy Sinus (Analgesic, Decongestant, Anti-Histamine), Sine-Aid (Sinus Headache), Dexatrim (Weight Loss), Buffered Aspirin (Analgesic), Mygranil (*Prescription for Migraine).

Volunteers were given the drug at doses as prescribed on the package and urine samples were collected at 2–4 hour intervals for a total of 24 hours from the time of ingestion of first dose.

The nicotine detection system is used by a subject for monitoring nicotine use. This method entails contacting the liquid sample with a solid phase impregnated with assay reagents including a color determinant, a buffer, a cyanogen releasing agent and a cyanogen halide forming agent, and detecting the formation of color as indicative of the presence of nicotine and/or nicotine metabolites. The terms nicotine and/or nicotine metabolites, solid phase, impregnated, color determinant, buffer, cyanogen releasing agent and cyanogen halide forming agent are used as defined above.

The term "contacting" is intended to include any procedure whereby the solid phase makes physical contact with the liquid sample. Examples of ways in which contact can be made include immersing, either manually or mechanically, the solid phase into a container which contains the liquid sample, or applying an aliquot of the liquid sample onto the solid phase. Preferably, one end of the solid phase is immersed into the liquid sample, such that the liquid initially makes contact with the color determinant. Then, by capillary action, the liquid sample moves vertically through the solid phase, sequentially making contact with the buffer, the cyanogen releasing agent and the cyanogen halide forming agent, or, sequentially making contact with the cyanogen releasing agent, the buffer and the cyanogen halide forming agent.

Preferably, the amount of sample applied to the strip and the manner in which the sample is applied to the strip are specified. It is preferable that the sample be contacted with only a portion of the strip, with capillary action drawing the sample through the strip and into contact with the various reagents of the strip. In the preferred strip (see examples), the end of the strip containing the color determinant is immersed in the sample with approximately ½ of the color determinant region being immersed. The remaining portions of the strip are not immersed. Also in the preferred assay (see examples), a sample of about 0.5–1.0 ml is contacted with the color determinant end of the strip. This is a sufficient volume to permit the sample to contact the reagents such that a color end product is produced, but not so much for example to reduce color intensity due to dilution, to reduce the effects of the buffer due to dilution, or to cause any of the reagents to be washed from the strip.

The term detecting the formation of color is intended to include any process whereby the presence or absence of color is determined. Such processes include visual detection and detection with instruments. The preferred method for detecting color formation is visual detection. The formation of color can be detected on the solid phase or in the liquid test sample. Preferably, color is detected on the solid phase. Depending upon the color determinant that is selected for the reaction assay, a particular color is formed if nicotine and/or nicotine metabolites are present in the test sample. When the preferred color determinant, diethyl thiobarbiturate, is used in the reaction assay, the presence of nicotine and/or nicotine metabolites in the test sample results in the formation of a pink color.

The assay is qualitative, in that the formation of any color indicates the presence of nicotine and/or nicotine metabolites. The assay is semi-quantitative or quantitative, in that the intensity of color formed on the solid phase is indicative of the amount of nicotine and/or nicotine metabolites present in the test sample. This would be desirable for distinguishing between a light or heavy smoker.

Preferably, the intensity of color formation from the reaction assay is compared to a standard. The standard may comprise a known quantity of nicotine and/or nicotine metabolites which is or has been contacted with a duplicate solid phase. The term "duplicate solid phase" is intended to include a solid phase that is essentially identical to the solid phase used in the reaction assay for the test sample, in terms of composition, size, shape and the impregnated reagents. The standard may be generated by performing an assay reaction with a solution containing a known concentration of nicotine and/or nicotine metabolites. The solution containing a known concentration of nicotine or nicotine metabolites also acts as a quality control of the test assay procedure.

The standard may also be a reference color chart which is generated to simulate the intensity of color formed when an assay reaction with a solution containing a known concentration of nicotine and/or nicotine metabolites is performed. For example, a standard representing 5–6 µg/ml and 12–15 µg/ml of nicotine and/or nicotine metabolites in urine can be used to identify light to moderate and heavy smokers, respectively. A negative control with 0 µg/ml of nicotine and/or nicotine metabolites also may be included. Alternatively, a semi-quantitative or quantitative determination of nicotine and/or nicotine metabolites may be made by measuring the optical densities in a spectrophotometer of the liquid test samples themselves, which also turn color as a result of the solid phase of this invention being immersed into the liquid test samples.

The nicotine detection system of this invention is capable of assaying unprocessed urine from smokers for the presence of nicotine and/or nicotine metabolites.

Preferably, the dried solid phase is packaged in a moisture proof material preferably formed into sleeves or pouches or aluminum or plastic canisters. Preferably, the canisters are equipped with tight-fitting moisture proof caps. A moisture proof material is desirable because moisture is an important factor in decreasing the stability of the reagent impregnated strip. Examples of moisture proof material include polypropylene coated aluminum foil, polypropylene polyethylene and aluminum foil. Preferably, the solid phase is packaged with a dessicant.

The following nonlimiting examples further illustrate the present invention.

Example 1

Preparation of Paper Strips

Absorbent Paper Grade #222 (Ahlstrom Filtration Co., Mount Holly Springs, Pa.) was cut to 7.5×25 cm size with letters "DG→" printed at 0.5 cm intervals along the length of the strip with an arrow pointing to the bottom of the 7.5 cm length. Only strips with sharp edges were used.

Example 2

Preparation and Application of Reagents to Paper Strips

40% chloramine-T was prepared by dissolving 40 gm of chloramine-T in warm water to make 100 ml final volume. This solution was kept warm at 65°–70° C. during dispensing. 100% potassium thiocyanate was prepared by dissolving 100 gm of potassium thiocyanate in water to make a final volume of 100 ml, while shaking under warm tap water. 2M citrate buffer was prepared by combining 23 ml of 2M citric acid with 27 ml of 2M trisodium citrate to give a pH of 4.2. 2.5% diethyl thiobarbiturate was prepared by dissolving 2.5 gm of diethyl thiobarbiturate in 100–80% ethanol to a final volume of 100 ml.

The blank strips from Example 1 were arranged on a strip support provided with shallow grooves to hold strips in place, with all the 'DG→' facing one side. Using an eight channel multipipetter, the reagents were applied onto the strips starting with chloramine-T, followed by potassium thiocyanate, citrate buffer, and finally, diethyl thiobarbiturate. The volumes of each of the reagents and the spacing of each on the strip were as follows: 40% chloramine-T—31.5 µl at the top end where 'DG→' was printed; 100% potassium thiocyanate—15 µl approximately 2 cm from the top; 2M citrate buffer pH 4.2—20 µl approximately 4 cm from the top; and 2.5% diethyl thiobarbiturate—20 µl at the bottom end of the strip.

After all the reagents were dispensed onto the strips, they were transferred onto a mesh tray and dried in a box attached with an exhaust fan. To enhance the drying process, warm air was blown into the box from the opposite end of the fan. The strips were dry in one hour. Since moisture is an important factor in the stability of the strips, they were generally dried for longer than 1½ hours.

Alternatively, reagents may be applied to a moving web of paper using 4 individual pumps (one per reagent). The resulting coated paper will have four discreet and continuous bands. The web of paper is then dried with hot air and slit into individual strips. The strips are oriented and collected in groups of a desired amount. A typical number of strips to group for packaging is 50.

Example 3

Packaging of Paper Strips

After the paper strips were dried, they were packaged individually in a moisture proof material such as polypropylene coated aluminum foil, polypropylene or polyethylene. The strips were packaged in small numbers, e.g., in sets of 5 per sleeve, each strip in its own pouch. Perforations were made between individual pouches so that single strips could be used without affecting the rest of the strips. On the side of the box containing the above package, a panel of colors was included to indicate one negative and two positive control colors. One of the positive colors corresponded to light to moderate smoker urine and the second color corresponded to heavy smoker urine. The packaged strips remain stable in the original packaging for at least a year at refrigerator temperature.

Alternatively, the strips are collected in groups and placed in an aluminum or plastic canister. The canister is sealed using a plastic cap that is equipped with a dessicant pack. The dessicant pack is exposed to the inside of the canister and controls the humidity within the canister.

Example 4

Use of Paper Strips for Assaying Urine Samples for the Presence of Nicotine and Nicotine Metabolites Approximately 0.5 ml of urine was pipetted into a 13×100 mm tube. The package containing the reagent impregnated paper strip was cut open at the top and the strip was taken out with forceps and dropped into the urine sample with the arrow pointing downwards. It was allowed to stand for 15–30 minutes, and any color changes were observed. Urine containing no nicotine or nicotine metabolites did not change the color of the strip. The presence of nicotine and its metabolites in a urine sample gave a pink color, both on the strip and in the solution. The presence or absence of cotinine, a nicotone/metabolite was independently verified using an enzyme immunoassay (EIA). The color was stable for almost an hour, after which it started to fade. Closing the tubes with a cap improved the final color intensity slightly.

Example 5

EIA Assays From the Urine of a Person Smoking One Cigarette

EIA assays were performed as described in Bjercke et al., *The Journal of Immunological Methods*, 90, (1986), pp. 203–213, the contents of which is expressly incorporated by reference, on urine samples taken at various times from a person who had smoked one cigarette.

TABLE 2

| Time Elapsed After Smoking | Reagent Impregnated Paper Strip Test | EIA Cotinine (µg/ml) |
| --- | --- | --- |
| 0 hours | − | 0.0 |
| 3 hours | − | 0.023 |
| 4 hours | + | 0.160 |
| 5 ½ hours | + | 0.120 |

Example 6

Comparison of Paper Strip and EIA Assays

The urine from 8–10 nonsmokers, light smokers, moderate smokers and heavy smokers was tested for the presence of nicotine and/or nicotine metabolites. Paper strip assays were performed as described in Example 4, and EIA assays were performed as described in Example 5.

TABLE 3

| Non-Smokers | Reagent Impregnated Paper Strip Test | EIA Cotinine (µg/ml) |
|---|---|---|
| 1 | – | 0.08 |
| 2 | – | 0.12 |
| 3 | – | 0.028 |
| 4 | – | *0.07 |
| 5 | – | N.D. |
| 6 | – | *0.07 |
| 7 | – | 0.0 |
| 8 | – | 0.0 |

*known secondary smoke exposure

TABLE 4

| Light Smokers | Reagent Impregnated Paper Strip Test | EIA Cotinine (µg/ml) |
|---|---|---|
| 1 | L | 0.7 |
| 2 | L | 2.2 |
| 31 | L | 0.64 |
| 3 | | |
| 4 | L | 0.20 |
| 5 | L | 2.00 |
| 6 | L | 1.2 |
| 7 | L | 0.7 |
| 8 | L | 1.4 |

(4/8 Subjects Self-Reported Consumption of 3–5 Cigarettes/Day)

TABLE 5

| Moderate Smokers | Reagent Impregnated Paper Strip Test | EIA Cotinine (µg/ml) |
|---|---|---|
| 1 | M | 1.0 |
| 2 | M | 2.3 |
| 3 | M | 1.1 |
| 4 | M | N.D. |
| 5 | M | 1.1 |
| 6 | M | 1.6 |
| 7 | M | 1.4 |
| 8 | M | 2.0 |
| 9 | M | 2.3 |

(6/9 Subjects Self-Reported Consumption of 1 Pack/Day)

TABLE 6

| Heavy Smokers | Reagent Impregnated Paper Strip Test | EIA Cotinine (µg/ml) |
|---|---|---|
| 1 | H | 4.0 |
| 2 | H | 7.6 |
| 3 | H | 4.0 |
| 4 | H | 2.1 |
| 5 | H | 3.7 |
| 6 | H | 2.6 |
| 7 | H | 2.5 |
| 8 | H | 3.2 |
| 9 | H | 5.6 |
| 10 | H | 8.0 |

(8/10 Subjects Self-Reported Consumption of 1–2 Packs/Day)
L = light; M = moderate; and H = heavy
The L, M, and H designations were determined by observing the intensity of the pink color.

Example 7

Sublingual Tablets

Sublingual tablets are made in accordance with the formulation set forth in Table 7 and Table 8 below.

TABLE 7

| | |
|---|---|
| Lobeline Sulfate | 2.5 mg |
| Mannitol, USP (DC grade) | 31.5 mg |
| Microcryst. Cellulose | 40.35 mg |
| Sodium Starch Glycolate NF | 2.6 mg |
| Sodium Saccharin, USP | 0.5 mg |
| Flavor S.D. Peppermint, FCC | 0.75 mg |
| Magnasweet MM 188M | 0.5 mg |
| Vanilla flavor #800 | 0.2 mg |
| D&C Yellow #10, Aluminum Lake | 0.2 mg |
| Magnesium stearate, NF | 0.5 mg |
| Aerosil 200 | 0.4 mg |
| TOTAL | 80 mg |

TABLE 8

| COMPONENT | WEIGHT PER DOSE (mg) |
|---|---|
| Lobeline sulfate | 7.50 |
| Mannitol | 30.30 |
| Microcrystalline cellulose (FMC) 4.00 | 34.00 |
| Sodium starch glycolate (EXPLS TAB Mendell) | 2.60 |
| Magnesium stearate NF | 0.50 |
| Colloidal silicon dioxide (Aerosil 200) | 0.40 |
| Sodium saccharin (Mallinckrodt) | 2.00 |
| Aspartama (Neutrasweet) | 4.00 |
| Peppermint (Virginia Dare HF82 SD #517) | 0.40 |
| Vanilla (Virginia DAre 800 NAT) | 0.30 |
| MAFCO Magnasweet 188M | 0.25 |
| Prosweet #560 (MM54) | 0.75 |
| Chocolate Flavor #682 | 2.00 |
| D&C Yellow #10 | 0 |
| TOTAL (mg) | 85.00 |

The formulation set forth in Table 8 represents a preferred sublingual tablet formula. Individuals skilled in the art will recognize that modifications to the formulation can be readily made.

The preferred formulation features a tablet with 7.5 mg lobeline sulfate. This dosage can be varied to provide 0.6 mg or smaller and as much as 10.0 mg or more. However, lobeline amounts in less than 0.6 mg may require the administration of more than one tablet to obtain the desired effect. Higher doses could, however, be required for individuals highly addicted to nicotine.

Other nicotine substitutes such as arecoline, isoarecolone, anabasine and cytisine may be substituted for lobeline sulfate. Individuals skilled in the art would determine the appropriate amounts of the nicotine substitute based on the lobeline sulfate amounts.

In the above formulation, mannitol, sodium saccharin, peppermint, magnasweet and vanilla are flavoring agents which are capable of masking the bitter taste of lobeline. The flavoring agents may be deleted without sacrificing efficacy. However, patient compliance may be more difficult. Flavorings may be altered to suit individual needs and tastes.

D&C yellow is used as a colorant. The colorant may be readily deleted or substituted with other dyes.

Magnesium stearate and Aerosil-200 are lubricants to release the tablet from press equipment. These ingredients may be substituted or deleted entirely depending on the manufacturing process.

Microcrystalline cellulose, mannitol and sodium starch glycolate provide the tablet core. The cellulose and starch facilitate binding the core ingredients and facilitate tablet disintegration in the presence of moisture. The relative amounts of these ingredients may be altered to adjust the disintegration of the tablet.

Quantities of all ingredients are weighed and all the ingredients, other than mannitol and Avicel, are passed through a 80 mesh stainless steel sieve. The materials are blended in a suitably sized polythene bag for about five minutes and transferred to suitable blender, such as a PK Blender. The required quantities of mannitol and Avicel are passed through a 40 mesh stainless steel sieve and added to the PK Blender with the other ingredients. The mixture is blended in the PK Blender for 10 minutes and unloaded. A sample of the blend is subjected to inspection for potency and other quality determining criteria. The bulk density is determined on the blend using bulk density apparatus set for 100 taps. The tablet press is set for the designated punches and the blend is compressed at 80 mg tablet weight.

Tablets are administered by placing a single tablet under the tongue. The tablet is allowed to disintegrate and release the nicotine substitute, lobeline. The nicotine substitute, lobeline is absorbed by the sublingual mucosa.

Example 8

Sublingual and Nasal Solutions

Sublingual and nasal solutions are made in distilled sterile water in accordance with the formulation set forth in Table 9.

TABLE 9

| Lobeline Sulfate | 2.0 to 20.0 mg/ml |
|---|---|
| Sodium Chloride | 0.9% |
| Benzalkonium Chloride | 0.1 to 0.2% |

The formulation set forth in Table 9 represents a preferred sublingual or nasal solution or a solution for forming a fine mist for administration to the pulmonary tissues. Individuals skilled in the art will readily recognize that modifications to the formulation can readily be made.

Other nicotine substitutes such as arecoline, isoarecolone, anabasine and cytisine may be substituted for lobeline sulfate. Individuals skilled in the art would determine the appropriate amounts of these other nicotine substitutes based on the lobeline sulfate dosage.

In the formulation above, sodium chloride is used to bring the solution to isotonicity. Such solutions are more comfortable for users; however, sodium chloride may be deleted if desired.

Benzalkonium chloride is used as a preservative. Preservatives may be omitted where storage and long term use are not important considerations. Benzalkonium chloride may be readily substituted with other preservatives which are recognized as safe and effective.

The nicotine substitute containing solutions of the present invention may be administered to the nasal or sublingual mucosa by way of a spray bottle. A nasal spray bottle, typically comprises a collapsible container vessel, a nasal applicator and a cap. The nasal applicator is sized to be received in the nasal passages of the nose. Nasal applicator has an opening to release a spray or mist of a liquid (not shown) held in vessel.

The spray bottle is designed to deliver an individual dose with one to three compressions of the bottle to deliver an effective dose of nicotine substitute to the nasal mucosa. The concentration of the nicotine substitute and lobeline in the liquid is preferably between 2.0 mg and 20.0 mg per ml in order to provide an effective dose upon one to three sharp compressions of the bottle. Bottle is designed to administer a range of liquid volume from 0.05 to 0.20 ml as a mist or spray. Preferably, one sharp compression delivers approximately 0.1 ml of liquid. Larger volumes are possible; however, larger volumes may allow the liquid to be received as a non-uniform coating of the nasal mucosa leading to variability in the amount of lobeline absorbed by the nasal mucosa. In addition, larger volumes may also have difficulty being retained on the nasal mucosa and run from the nasal passages, reducing the effectiveness of the administration.

Individuals would use the nasal spray upon encountering a strong desire for nicotine. The spray would be administered to one or both nostrils by placing the nasal applicator in a nostril and making one to three sharp compressions on vessel.

The liquid containing a nicotine substitute may also be applied to the nasal or sublingual mucosa in the form of drops.

Preferably, for applications to the nasal mucosa the liquid has a concentration of 2.0 mg and 20.0 mg/ml lobeline free-base equivalent to allow an effective dosage with 2–6 drops in one or more nostrils. Lower concentrations are possible; however, a large volume of drops may be required to produce a desired effect. A large liquid volume may be difficult to retain in the nasal passages. Higher concentrations are possible; however, the small volume of drops may be difficult to dose accurately.

Individuals would use the drops upon encountering a strong desire for nicotine. The drops are administered to one or both nostrils by tilting the head back and placing the drops in the nasal passages. The drops are then inhaled or withdrawn up the nasal passages.

With respect to liquids for administration to the sublingual mucosa, a liquid having 0.6 to 7.5 mg equivalent of lobeline free-base is administered under the tongue. Individuals would use the dropper by withdrawing a dose of the nicotine substitute containing liquid from the dropper bottle and administering the drops to the sublingual mucosa and holding the liquid in place as lobeline is absorbed through the sublingual mucosa. Preferably, the liquid is flavored to improve patient acceptance.

The liquid is preferably held in a dropper bottle or the functional equivalent.

Example 9

This Example features the preparation of nicotine substitute powders and liquids for administration to pulmonary and buccal tissues. Powders of nicotine substitutes are finely ground and pulverized into 1–8 μm sized particles, with a mass median diameter of 3 and 6 μm. Such particles are combined with similarly sized excipients and loaded into propellant containing cartridges.

The excipients may comprise lubricants such as isopropyl myristate, light mineral oil and other materials to allow slippage of the particles on the valve components. Substitutes may be used to facilitate dispersal of particles. Other dispersing agents such as sorbitan trioleate, oleyl alcohol, oleic acid, lecithin and corn oil may be used to keep particles from agglomerating. However, excipients must be used sparingly in that the pulmonary tissues are sensitive to nonaqueous materials and particulates.

Liquids for use in inhalers have a nicotine substitute dissolved in an aqueous medium as described with respect to sublingual and nasal solutions. These solutions are combined with suitable propellants and loaded into cartridges.

Typical inhalers have a mouthpiece, valve and a pressurized cartridge containing the nicotine substitute and propellants. The subject uses the inhaler by inserting the mouthpiece in the mouth and closing the lips about the mouthpiece. The subject breathes in as the inhaler is activated. The subject continues to breathe in slowly and deeply, and hold his or her breath for ten seconds. The subject then breathes out slowly through the nose.

Powder and liquid aerosols are well characterized in the pharmaceutical arts. See Remington's Pharmaceutical Sciences, p. 1694–1712, Mack Publishing Company, Easton, Pa. (1990).

Example 10

Physical constraint modulation systems are disclosed in U.S. Pat. No. 5,403,595 (incorporated herein by reference). These systems comprise bioresorbable polymers for the delivery of nicotine substitutes, and transdermal patches.

Example 11

This example describes the use of lobeline sublingual tablets of varying strength. Sublingual tablets were prepared in accordance with Example 7. These sublingual tablets comprised 2.5 mg 1-lobeline sulfate, 5.0 mg 1-lobeline sulfate, 7.5 mg 1-lobeline sulfate. A placebo sublingual tablet was formed incorporating an inert material. These tablets were administered to 22 subjects who regularly smoked nicotine cigarettes. The strength and number of tablets administered per day determined the total daily dose.

The subjects spent two nights in the clinic and abstained from smoking over the full time. Subjects entered the clinic at noon on Day 1 and immediately ceased tobacco consumption. At 7:00 a.m. the next morning they started taking either placebo or 1-lobeline sulfate sublingual tablets, which they continued to take periodically on the dose group to which they belonged and the strength of tablet.

Figure 4:
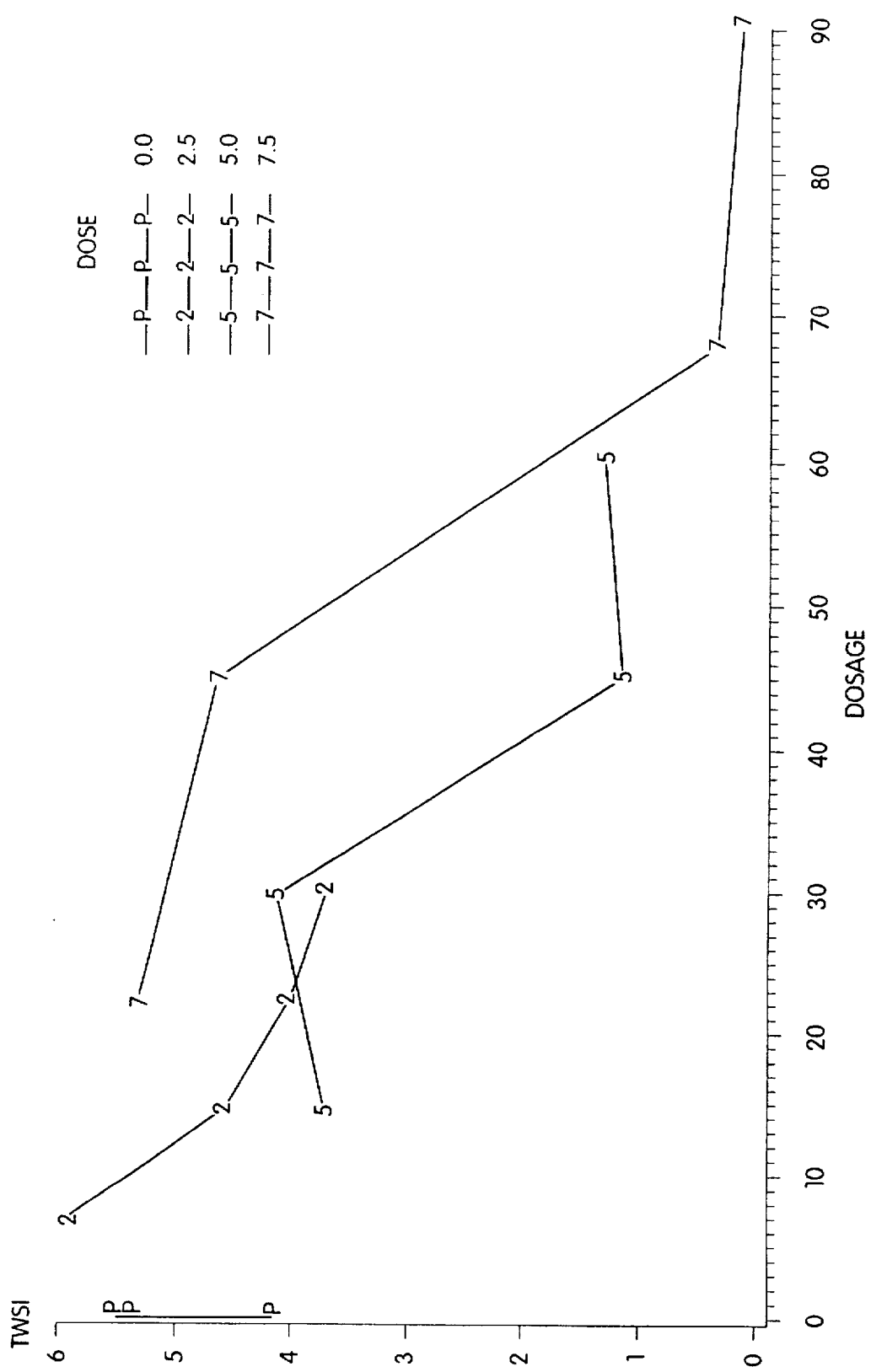
FIG. 4 depicts graphically tobacco withdrawal symptoms index scores averaged for each individual plotted against the amount of lobeline sulfate administered per day.

Tobacco Withdrawal Syndrome Index (TWSI) scores were taken periodically throughout the day. The TWSI is a system for evaluating symptoms of tobacco smoking withdrawal on a numerical 0–4 scale. The components of TWSI which were evaluated comprised anxiety, anger, craving for a cigarette, restlessness and difficulty concentrating. The TWSI scores were obtained in three separate 42–44 hour sessions, one in each of three consecutive weeks. The total amount of lobeline sulfate administered sublingually per day was plotted against the Tobacco Withdrawal Syndrome Index (TWSI) score averaged for each subject. In FIG. 4, "P" is used to indicate the use of placebo sublingual tablets containing no lobeline. The line marked with "2" indicates the response to the use of 2.5 mg L-lobeline sulfate sublingual tablets. The line marked "5" indicates the response to 5.0 mg L-lobeline sulfate sublingual tablets. And, the line marked "7" indicates the response to 7.5 mg L-lobeline sulfate sublingual tablets. These results suggest a marked reduction in nicotine withdrawal symptoms with increasing doses of L-lobeline sulfate. These results suggest that an effective amount is approximately 45–90 mg of L-lobeline sulfate administered sublingually per day.

Example 12

This example describes a study involving the use of lobeline sulfate sublingual tablets with 156 smokers.

These smokers were randomly divided into four groups. One group received 30 mg 1-lobeline sulfate/per day administered as 5 mg 1-lobeline sulfate sublingual tablets 6 times per day. A second group received 45 mg 1-lobeline sulfate/per day administered as 5 mg 1-lobeline sulfate sublingual tablets nine times per day. A third group received 67.5 mg 1-lobeline sulfate/per day administered as 7.5 mg 1-lobeline sulfate sublingual tablets 9 times per day. A fourth group received a placebo administered nine times per day. Each individual of each group received brief (5 to 10 minutes) once a week behavioral counseling.

Lobeline tablets were made in accordance with Example I. The lobeline sulfate tablets were formulated to mask the taste of lobeline. The placebo tablets were formulated to imitate the flavor of lobeline tablets.

The results of the study suggest that lobeline, administered sublingually, in rapid disintegrating tablets, can be administered safely with no clinically significant adverse effects. The results of the study suggest that lobeline, administered sublingually, in rapid disintegrating tablets is effective to alleviate tobacco withdrawal symptoms and reduce the number of cigarettes smoked per day.

Results of the study with respect to smoking activity are summarized in Table 10 below:

TABLE 10

NicErase ™-SL PHASE 2b: SMOKING ACTIVITY

| Group | Cigarettes Smoked Per Week | |
|---|---|---|
| | pre-Study | Study Weeks 3–6 |
| All Subjects Minus Dropouts | | |
| Placbo (n = 29) | 214 | 45 |
| Low (n = 17) | 215 | 38 |
| Medium (n = 22) | 199 | 69 |
| High (n = 18) | 203 | 34 |
| ≧77% Compliant to Therapy | | |
| Placebo (n = 19) | 223 | 39 |
| Low (n = 6) | 224 | 41 |
| Medium (n = 13) | 198 | 49 |
| High (n = 9) | 215 | 13 |
| 100% Compliant to Therapy | | |
| Placebo (n = 9) | 233 | 60 |
| Low (n = 5) | 244 | 48 |
| Medium (n = 5) | 228 | 63 |
| High (n = 2) | 257 | 1 |

Consistent with FDA guidelines, treatment efficacy was evaluated during post cessation weeks 3–6 of the study. The results of the low and medium doses of lobeline are not as clear as the high dose due to the small enrollment number of this study. The low and medium doses may also be less than optimal for a percentage of the population. The low and medium dose results are, therefore, more variable. However, these results do suggest that lobeline administered sublingually is more effective than a placebo. The results suggesting a reduction of cigarettes smoked, from well over 200, down to one to 13, with respect high doses of lobeline, is striking.

Results of the study with respect to abstinence rates are summarized in Table 11 below:

TABLE 11

NicErase ™-SL PHASE 2b: ABSTINENCE RATES

| Group | n | Successes | Failures | Dropouts | Efficacy for All Subjects % | Efficacy for All, Minus Dropouts % |
|---|---|---|---|---|---|---|
| All Subjects | | | | | | |
| Placebo | 38 | 8 | 28 | 2 | 21 | 22 |
| Low | 39 | 7 | 18 | 14 | 18 | 28 |
| Medium | 39 | 7 | 22 | 10 | 18 | 24 |
| High | 38 | 6 | 17 | 15 | 16 | 26 |
| ≧77% Compliant to Therapy | | | | | | |
| Placebo | 24 | 5 | 19 | | | 21 |
| Low | 10 | 4 | 6 | | | 40 |
| Medium | 18 | 4 | 14 | | | 22 |
| High | 14 | 5 | 9 | | | 36 |
| 100% Compliant to Therapy | | | | | | |
| Placebo | 14 | 4 | 10 | | | 29 |
| High | 7 | 2 | 5 | | | 29 |
| Medium | 8 | 2 | 6 | | | 25 |
| High | 3 | 1 | 2 | | | 33 |

Smoking activity, expressed either as the number of cigarettes smoked or as total abstinence from smoking, was clearly reduced for those subjects who complied with therapy to an extent of taking at least 77% of their recommended doses. With respect to Table 11, within those individuals who were identified as 100% compliant, there is one individual who received high dose lobeline and who smoked one cigar and as a result is identified as a failure This individual apparently did not understand that he was not allowed to smoke a cigar and still be considered abstinent from smoking. However, had this individual not smoked that one cigar, the efficacy of high dose lobeline would be demonstrating efficacy in promoting abstinence.

Figure 5:
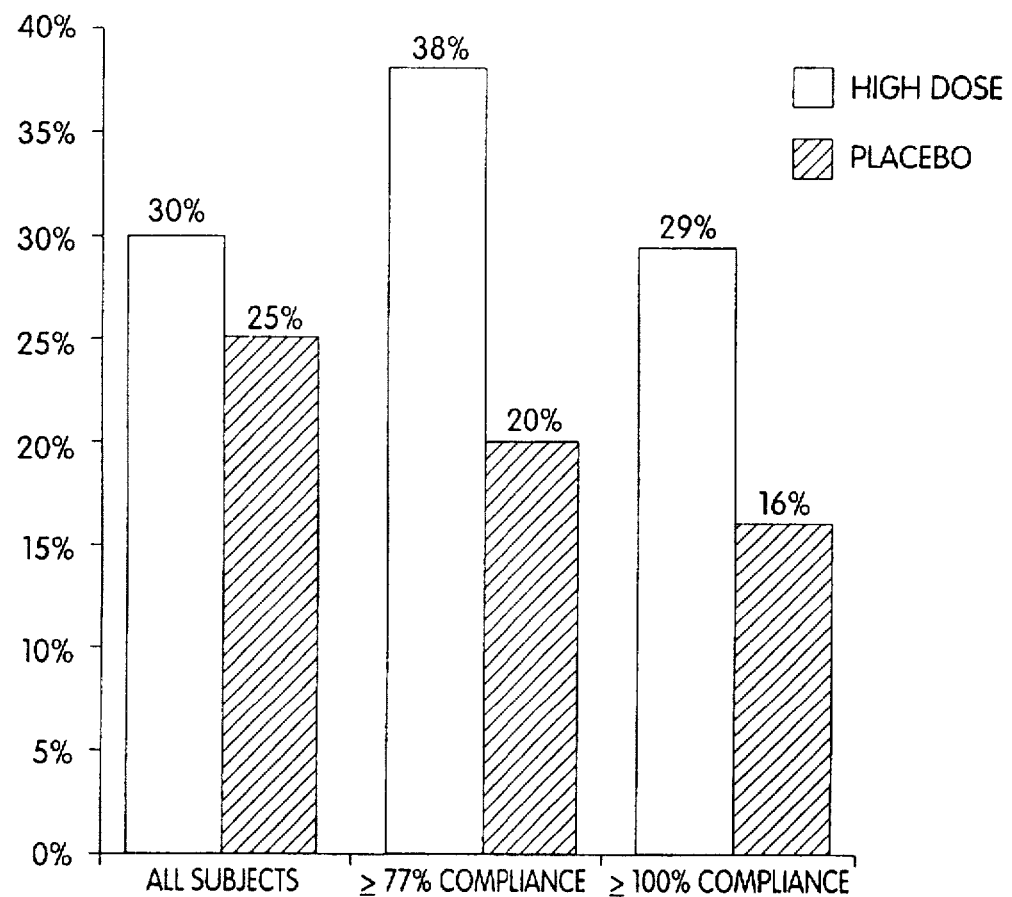
FIG. 5 graphically depicts the reduction of nicotine withdrawal symptoms as a function of compliance with a therapeutic regimen comprising the method of the present invention.

The results with respect to smoking withdrawal scores, for the high dose lobeline group compared to placebo is set forth in FIG. 5.

The difference between the placebo and the lobeline group became greater as compliance to therapy increased, again indicating that lobeline reduces tobacco withdrawal symptoms. The results of FIG. 4 are striking in demonstrating a reduction in smoking withdrawal symptoms.

Example 13

Individuals would monitor their abstinence from nicotine use while using a nicotine substitute by testing their urine as set forth in Example 4–6. The nicotine detection system would not detect the nicotine substittite allowin an accurate assessment of abstinence.

This example describes a study involving the use of the nicotine detection system in eight cigarette smokers. They were randomly divided into two groups. One group was placed on Lobeline sulfate sublingual tablets (DESC) 7.5 mg and the rest were on placebos. All subjects received a brief individual smoking cessation counseling once a week. Carbon monoxide (CO) level was monitored at each visit. Urine samples were collected durina these visits and nicotine and/or nicotine melabolite level was determined using the device as described in Example 4. Nicotine and cotinine levels of all the urine samples were determined by gas chromatograohy (GC). Information regarding the number of cigarettes smoked per week was obtained through self reporting The results of the study are presented in Table 12. A total of 50 urine samples were collected during a period of seven visits. Overall, a good correlation is observed between the cotinine v alues of urine samples. The results of the nicotine monitoring device and carbon monoxide in the exhaled air of the corresponding time point.

TABLE 12

| Subject #/ Composition Detected | Visit 4/Visit 8 | Visit 5/Visit 9 | Visit 6/Visit 10 | Visit 7 |
|---|---|---|---|---|
| 153 (P)/ Nicotine (ng/ml) | 933/294 | <10.0/2050 | 31.4/2620 | 73.2 |
| 153 (P)/ Cotinine (ng.ml) | 2700/1440 | 12.2/1460 | 378/1930 | 778 |
| 153 (P)/ Carbon Monoxide | 22/19 | 1/15 | 3/19 | 5 |
| 153 (P)/ No. of Cigarettes | 163.33/35 | 3/42 | 8/52 | 21 |
| 153 (P)/ Example 4 | 1/1 | 0/1 | <1/1 | <1 |
| 154 (P)/ Nicotine (ng/ml) | 2070/163 | <10/108 | 26.8/106 | 86.5 |
| 154 (P)/ Cotinine (ng/ml) | 2430/1070 | 31.7/1090 | 278/1030 | 759 |
| 154 (P)/ Carbon Monoxide | 26/10 | 4/14 | 7/14 | 10 |
| 154 (P)/ No. of Cigarettes | 161/22 | 2/19 | 18/19.6 | 17 |
| 154 (P)/ Example 4 | 1/1 | 0/2 | <1/2 | 1 |
| 155 (L)/ Nicotine (ng/ml) | 1390/<10.0 | 19.9/10.3 | No Visit/21.1 | <10.0 |
| 155 (L)/ Cotinine (ng/ml) | 1670/134 | 64.4/362 | No Visit/127 | 139 |
| 155 (L)/ Carbon Monoxide | 15/6 | 2/4 | 4/4 | 3 |
| 155 (L)/ No. of Cigarettes | 109.67/0 | 0/0 | 1/0 | 0 |
| 155 (L)/ Example 4 | 1/0 | 0/0 | No Visit/0 | 0 |
| 156 (P)/ Nicotine (ng/ml) | 1420/<10.0 | 13.3/<10.0 | <10.0/10.2 | 28.4 |
| 156 (P)/ Cotinine (ng/ml) | 2540/25.1 | 312/<10.0 | 16.4/<10.0 | 26.6 |
| 156 (P)/ Carbon Monoxide | 19/3 | 2/1 | 2/3 | 1 |
| 156 (P)/ No. of Cigarettes | 115.53/0 | 59/0 | 0/0 | 0 |
| 156 (P)/ Example 4 | 1/0 | 0/0 | 0/0 | 0 |
| 157 (P)/ Nicotine (ng/ml) | 1460/<10.0 | <10.0/ND | <10.0/ND | <10.0 |
| 157 (P)/ Cotinine (ng/ml) | 1370/<10.0 | 29.3/<10.0 | <10.0/<10.0 | <10.0 |
| 157 (P)/ Carbon Monoxide | 30/5 | 2/2 | 4/4 | 3 |

TABLE 12-continued

| Subject #/ Composition Detected | Visit 4/Visit 8 | Visit 5/Visit 9 | Visit 6/Visit 10 | Visit 7 |
|---|---|---|---|---|
| 157 (P)/ No. of Cigarettes | 178.53/0 | 21/0 | 0/0 | 0 |
| 157 (P)/ Example 4 | 1/0 | 0/0 | 0/0 | 0 |
| 158 (L)/ Nicotine (ng/ml) | 1310/No Visit | <10.0/ No Visit | No Visit/2010 | 747 |
| 158 (L)/ Cotinine (ng/ml) | 2010/No Visit | 72/No Visit | No Visit/2060 | 1620 |
| 158 (L)/ Carbon Monoxide | 21/No Visit | 4/No Visit | No Visit/28 | 22 |
| 158 (L)/ No. of Cigarettes | 266/Dropout | 32/Dropout | 121/Dropout | Dropout |
| 158 (L)/ Example 4 | 2/No Visit | <1/No Visit | No Visit/2 | 1 |
| 159 (P)/ Nicotine (ng/ml) | 1750/No Visit | 579/479 | 284/1590 | 1330 |
| 159 (P)/ Cotinine (ng/ml) | 1070/No Visit | 744/579 | 258/1840 | 660 |
| 159 (P)/ Carbon Monoxide | 29/No Visit | 24/39 | 16/37 | 27 |
| 159 (P)/ No. of Cigarettes | 192.5/23 | 22/23 | 23.8/23 | 23 |
| 159 (P)/ Example 4 | 1/No Visit | 1/1 | 1/2 | 1 |
| 160 (L)/ Nicotine (ng/ml) | 400/827 | 61/No Visit | 10.6/420 | 1530 |
| 160 (L)/ Cotinine (ng/ml) | 1350/662 | 507/No Visit | 336/1380 | 1130 |
| 160 (L)/ Carbon Monoxide | 19/28 | 3/No Visit | 5/30 | 25 |
| 160 (L)/ No. of Cigarettes | 204.17/170 | 33/193 | 45/161 | 88 |
| 160 (L)/ Example 4 | 1/1 | 1/No Visit | <1/1 | 1 |

As used above, the designation "ND" indicates that no nicotine was detected; The designation "P" indicates placebo treatment, and "L" indicates active ingredient, lobeline sulfate treatment.

The advantages of using a nicotine metabolite monitoring device in studies where the replacement therapy used in a nicotine substitute is further evidenced in this study. For example, the cotinine values of urine samples from subjects #156 and #157 dropped sionificantlv from their first visit to the next and remain very low throughout the rest of the study period. Nicotine/metabolite monitoring device detected all these samples with almost 100% accuracy. (Exception is visit #5 of subject #156.) These results also suggest the poor correlation between the self-reported cigarette consumption and the level of cotinine in the urine. Whereas the correlation between the cotinine concentration of urine samples and the results from the nicotine/metabolite monitoring device is very high, indicating the need for a biochemical marker for monitoring nicotine consumption as a more reliable tool.

Thus, while preferred embodiments of the present invention have been described, the present invention is capable of variation and modification and, therefore, the present invention should not be limited to the precise details set forth, but should include such changes and alterations as fall within the purview of the following claims. Each of the references disclosed above is hereby incorporated by reference.

What is claimed is:

1. A method of treating nicotine withdrawal symptoms, comprising:

administering to a subject an effective amount of a nicotine substitute prior to or during a period in which the subject is experiencing nicotine withdrawal symptoms, to alleviate the subject's desire for nicotine; and monitoring said subject for the presence of nicotine and nicotine metabolite in a biological sample of the subject with a nicotine detection system.

2. The method of claim 1 wherein the equivalent of 0.6 to 10.0 mg lobeline free base in the form of a nicotine substitute is administered per dose.

3. The method of claim 1 wherein the nicotine substitute is arecoline, isoarecolone, anabasine, cystine, and analogs thereof and pharmaceutically acceptable salts thereof.

4. The method of claim 1 wherein said nicotine substitute is lobeline, lobeline analogs or a pharmaceutically acceptable salt of lobeline or a lobeline analog.

5. The method of claim 4 wherein said nicotine substitute is administered by a physical constraint modulation system.

6. The method of claim 1 wherein said nicotine substitute is administered as a sublingual tablet.

7. The method of claim 1 wherein said nicotine substitute is administered as a liquid, said nicotine substitute dissolved in said liquid as a soluble salt.

8. The method of claim 7 wherein said nicotine substitute is administered as a nasal spray.

9. The method of claim 7 wherein said nicotine substitute is administered as nasal drops.

10. The method of claim 7 wherein said nicotine substitute is administered as a sublingual liquid.

11. The method of claim 1 wherein said nicotine substitute is administered as a powder or a liquid mist to one or more of the following tissues consisting of the pulmonary tissues and buccal mucosa.

12. The method of claim 1 wherein said nicotine substitute is administered in a dose of 30–140 mg per day.

13. The method of claim 1 wherein said monitoring comprises having a porous support, and said porous matrix having a receiving section and a wicking section, said receiving section for contacting the biological sample and said wicking section for receiving liquid through capillary action from said receiving section to define a flow of fluid, said porous matrix impregnated with reagents, said reagents comprising a color determinant, a buffer, a cyanogen releasing agent and a cyanogen halide forming agent; each of said reagents occupying a separate and distinct area of the matrix to prevent interactions between said reagents, each of said areas having a position, said order defined by the flow of liquid in the porous matrix in which the first reagent to come in contact with the biological sample is said color determinant, followed by said buffer, followed by said cyanogen releasing agent and followed by said cyanogen halide forming agent, or said color determinant is followed by said cyanogen releasing agent, followed by said buffer, followed by said cyanogen halide agent; said porous matrix absorbing the biological sample in the receiving section and wicking liquid through the wicking section to bring said cyanogen releasing agent and cyanogen halide forming agent together to form a first reaction product in the presence of said buffer, which buffer maintains said first reaction product within a pH range; said first reaction product reacts with nicotine and nicotine metabolite, if present, to form a second reaction product, said second reaction product is maintained within a pH range by said buffer; said second reaction product reacting with said color determinant to form a third reaction product, which third reaction product is maintained within a pH range by said buffer, and is detectable by a change in color; and said method further comprises the step of monitoring said solid support for a change in color indicative of the presence of nicotine and nicotine metabolites.

14. The method of claim 1 wherein the nicotine substitute is selected from the group consisting of anti-anxiety agents, antidepressants, antiobsessional agents, and antipsychotic agents.

15. As an article of manufacture, a kit for treating nicotine withdrawal symptoms and monitoring nicotine use comprising:
   an effective amount of a nicotine substitute for administration to a subject, said nicotine substitute for alleviating nicotine withdrawal symptoms; and
   a plurality of nicotine detection systems for detecting the presence of nicotine in a biological sample.

16. The kit of claim 15 wherein said effective amount of a nicotine substitute is the equivalent of 0.6 to 7.5 mg of lobeline free base per dose.

17. The kit of claim 15 wherein said nicotine substitute is arecoline, isoarecoline, anabasine, cystine, and analogs thereof and pharmaceutically acceptable salts thereof.

18. The kit of claim 15 wherein said nicotine substitute is lobeline, a lobeline analog or a pharmaceutically acceptable salt of lobeline or a lobeline analog.

19. The kit of claim 15 wherein said nicotine substitute is held in a sublingual tablet.

20. The kit of claim 15 wherein said nicotine substitute is held or dissolved in liquid.

21. The kit of claim 15 wherein said liquid is held in a spray bottle for administration to the nasal mucosa.

22. The kit of claim 20 wherein said liquid is held in a dispensing bottle for administration to the nasal or sublingual mucosa.

23. The kit of claim 15 wherein said nicotine substitute is a powder or held in a liquid for administration to the pulmonary tissues and buccal mucosa.

24. The kit of claim 15 wherein said nicotine substitute is held in a physical constraint modulation system.

25. The kit of claim 16 wherein said nicotine detection system comprising a porous matrix, said porous matrix having a receiving section and a wicking section, said receiving section for contacting the biological sample and said wicking section for receiving the biological sample through capillary action from said receiving section to define a flow of fluid, said porous matrix impregnated with reagents, said reagents comprising a color determinant, a buffer, a cyanogen releasing agent and a cyanogen halide forming agent; said reagents having separate and distinct positions in the matrix to prevent interactions between said reagents, said position in any order defined by the flow of liquid in the porous matrix in which the first reagent in the flow of liquid is said color determinant, followed by said buffer, followed by said cyanogen releasing agent and followed by said cyanogen halide forming agent; said porous matrix absorbing the biological sample in the receiving section and wicking liquid through the wicking section to bring said cyanogen releasing agent and cyanogen halide forming agent together to form a first reaction product in the presence of said buffer, which buffer maintains said first reaction product within a pH range; said first reaction product reacts with nicotine and nicotine metabolites, if present, to form a second reaction product, said second reaction product maintained within a pH range by said buffer; said reaction product reacting with said color determination to form a third reaction product, which third reaction product is maintained within a pH range by said buffer, said third reaction product is detectable by a change in color, which change in color is indicative of the presence of nicotine and nicotine metabolites.

26. The kit of claim 15 wherein the nicotine substitute is selected from the group consisting of anti-anxiety agents, antidepressants, antiobsessional agents, and antipsychotic agents.

27. The kit of claim 15 wherein the plurality of nicotine detection systems is at least 4.

28. The kit of claim 15 wherein the plurality of nicotine detection systems is at least 6.

* * * * *